US006225531B1

(12) United States Patent
Kakitani et al.

(10) Patent No.: US 6,225,531 B1
(45) Date of Patent: May 1, 2001

(54) GLUCAN ELICITOR RECEPTOR, DNA MOLECULE CODING THEREFOR, FUNGUS-RESISTANT PLANTS TRANSFORMED WITH THE DNA MOLECULE AND METHOD FOR CREATING THE PLANTS

(75) Inventors: Makoto Kakitani; Naoyuki Umemoto, both of Yokohama; Isao Ishida, Takasaki; Akihiro Iwamatsu, Yokohama; Masaaki Yoshikawa, deceased, late of Sapporo, by Kuniko Yoshikawa, Masahi Yoshikawa, executors; Naoto Yamaoka, Sapporo, all of (JP)

(73) Assignee: Kirin Beer Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/094,557

(22) Filed: Jun. 15, 1998

Related U.S. Application Data

(63) Continuation-in-part of application No. 08/591,566, filed on Jul. 14, 1997, now abandoned, and a continuation-in-part of application No. PCT/JP96/03653, filed on Dec. 15, 1996.

(30) Foreign Application Priority Data

Jun. 17, 1994 (JP) ................................................... 6-136100
Dec. 15, 1995 (JP) ................................................... 7-347823

(51) Int. Cl.[7] ........................... C12N 15/82; C12N 15/29; C12N 5/04; A01H 5/00; C07H 21/04
(52) U.S. Cl. ......................... 800/301; 800/295; 800/312; 800/313; 800/317; 800/317.1; 800/298; 800/317.2; 800/317.3; 800/317.4; 800/279; 536/23.1; 536/23.6; 435/410; 435/418; 435/419; 435/320.1; 435/200; 530/378
(58) Field of Search ................................. 536/23.6, 23.1; 435/320.1, 69.1, 419, 468, 410, 200, 418; 800/278, 279, 298, 295, 301, 312, 313, 317, 317.1, 317.2, 317.3, 317.4; 530/378

(56) References Cited

PUBLICATIONS

Linthorst et al. Plant Cell. 1989. vol. 1:285–291.*
Carvalho et al. The EMBO J. 1992. vol. 11:2595–2602.*
Takeuchi et al. Plant Physiol. 1990. vol. 93:673–682.*
Spencer et al. Plant Mol Biology. 1992. vol. 18:201–210.*
Yoshikawa et al. Naturwissenschaften. 1993. vol. 80: 417–420. [ref.1].*
Yoshikawa et al. Physiol. Mol. Plant. Path. 1990. vol. 37:367–376. (ref. 2).*
Patent Abstracts of Japan, 6–321995, Nov. 22, 1994.
Frey et al., "Affinity Purification and Characterization of a Binding Protein for a Hepta–β–Glucoside Phytoalexin Elicitor in Soybean", Phytochemistry, vol. 32, No. 3, 1993, pp. 543–550.
Schmidt et al., "Specific Binding of a Fungal Glucan Phytoalexin Elicitor to Membrane Fractions from Soybean *Glycine max*", Proc. Natl. Acad. Sci. USA, vol. 84, Jun. 1987, pp. 4117–4121.
Keen, "Gene–for–Gene Complementarity in Plant–Pathogen Interactions", Annu. Reg. Genet., vol. 24, 1990, pp. 447–463.
Keen et al., β–1,3–Endoglucanase from Soybean Releases Elicitor–Active Carbohydrates from Fungus Cell Plant Physiol., vol. 71, 1983, pp. 460–465.
Sharp et al., "The Primary Structures of One Elicitor–Active and Seven Elicitor–Inactive Hexa(β–D–D–glucitols Isolated from the Mycelial Walls of *Phytophthora megasperma* f. sp. glycinea", The Journal of Chemistry, vol. 259, No. 18, Sep. 25, 1984, pp. 11321–11336.
Ham et al., "A Soybean Pathogenesis–Related Protein with β–1,3–Glucanase Activity Releases Phytoalexin Active Heat–Stable Fragments from Fungal Walls", Mole. Plant-Microbe Inter., vol. 4, No. 6, 1991, p. 545–552.
Yoshikawa et al., "A Specific Binding Site on Soybean Membranes for a Phytoalexin Elicitor Released from Cells Walls by β–1,3–Endoglucanase", Plant Cell Physiol., 34(8):1229–1237 (1993).
Keen et al., "Phytoalexin Elicitor Activity of Carbohydrates from *Phytophthora megasperma* f.sp. *glycinea* and Sources", Plant Physiol. (1983) 71, pp. 466–471.
Cheong et al., "Solubilization of Functional Plasma Membrane-Localized Hepta–β–Glucoside Elicitor–Binding Proteins from Soybean", Plant Physiol, (1993) 103:1173–1182.
Yoshikawa et al., "A Receptor on Soybean Membranes for a Fungal Elicitor of Phytalexin Accumulation", Plant Physiol., (1983)73:497–506.
Yoshikawa, et al., Elicitors: Their Significance and Primary Modes of Action in the Induction of Plant Cell Physiol., 34(8):1163–1173 (1993).

(List continued on next page.)

*Primary Examiner*—David T. Fox
*Assistant Examiner*—Ousama Zagmout
(74) *Attorney, Agent, or Firm*—Foley & Lardner

(57) ABSTRACT

A glucan elicitor receptor having an amino acid sequence as substantially shown in SEQ ID NO:1; DNA molecules containing nucleotide sequences coding for a glucan elicitor receptor having an amino acid sequence as substantially shown in SEQ ID NO:1, or fragments thereof; DNA molecules containing nucleotide sequences coding for a glucan elicitor receptor, which are incorporated in plasmid pER23-1, or fragments thereof; vectors containing the DNA molecules or fragments thereof; plant cells transformed with the DNA molecules or fragments thereof; a method for creating a plant having resistance to pathogenic fungi comprising incorporating the DNA sequence coding for a glucan elicitor receptor, or fragment thereof into a chromosome of a plant and expressing the gene in the plant; a plant having resistance to pathogenic fungi, the plant having the DNA molecule containing a nucleotide sequence coding for a glucan elicitor receptor, or its fragment transferred thereinto and expressing the gene; and methods for using the DNA molecule containing a nucleotide sequence coding for a glucan elicitor receptor, or fragment thereof.

16 Claims, 14 Drawing Sheets

OTHER PUBLICATIONS

Yoshikawa et al., "Release of a Soluble Phytoalexin Elicitor from Mycelial Walls of *Phytophthora megasperma sojae* by Soybean Tissues", Plant Physiol., (1981) 67:1032–1035.

Okinaka et al., "A Structural Model for the Mechanisms of Elicitor Release from Fungal Cell Walls by Plant β–1, 3–Engoglucanase", Plant Physiol., (1995) 109:839–845.

Cosio et al., "Identification of a High–Affinity Binding Protein for a Hepta–β–Glucoside Phytoalexin Elicitor in Soybean", Eur. J. Biochem., 204:1115–1123 (1992).

Keen, "Specific Elicitors of Plant Phytoalexin Production: Determinants of Race Specificity in Pathogens?", Science, vol. 187, pp. 74–75.

Yoshikawa, "Diverse Modes of Action of Biotic and Abiotic Phytoalexin Elicitors", Nature, vol. 257, No. 5680, Oct. 12, 1978, pp. 546–547.

Yoshikawa, "Molecular Mechanism of the Indution of Elicitor and Phytoalexin", (Partial Translation) Plant Cell Technology, vol. 2, No. 6, 1990, pp. 695–703 (abstract).

Yoshikawa et al., "Glyceollin: Its Role in Restriction Fungal Growth in Resistant Soybean Hyocotyls Infected *Phytophthora megasperma* var. *sojae*", Physiological Plant Pathology, 12:73–82 (1978).

Cheong et al., "A Specific, High–Affinity Binding Site for the Hepta–β–Glucoside Elicitor Exists in Soybean Membranes", The Plant Cell, vol. 3, Feb. 1991, pp. 137–147.

Cosio et al., "Solubilization of Soybean Membrane Binding Sites for Fungal β–Glucans that Elicit Phytoalexin Accumulation", FEBS Letters, vol. 264, No. 2, May 1990, pp. 235–238.

Cosio et al., "High–Affinity Binding of Fungal β–Glucan Fragments to Soybean (*Glycine max* L.) microsomal Fractions and Protoplasts", Eur. J. Biochem., 175:309–315 (1988).

Dixon, "Moleular Communication in Interactions Between Plants and Microbial Pathogens", Annu. Rev. Plant Physiol. Plant Mol. Biol., 41:339–67 (1990).

Potrykus, Ann. Review of Plant Physiol. 1991, vol. 42:205–225.

Napoli et al., The Plant Cell, 1989, vol. 2:278–289.

Schreiber et al., Accession No.: X17487, NCBI, Oct. 8, 1992.

Hahn et al., "Characterization of hepta–β–glucoside Elicitor–Binding Protein(s) in Soybean," Biochem. Soc. Symp., vol. 60, 1994, pp. 101–112.

\* cited by examiner

SDS-POLYACRYLAMIDE GEL ELECTROPHORESIS

1: Mono Q ACTIVE FRACTION
2: PASS-THROUGH FRACTION FROM MALTOSE-COUPLED GLASS GEL
3: ELUTION FRACTION FROM ELICITOR-COUPLED GLASS GEL
3: ER: ELICITOR RECEPTOR

FIG. 2
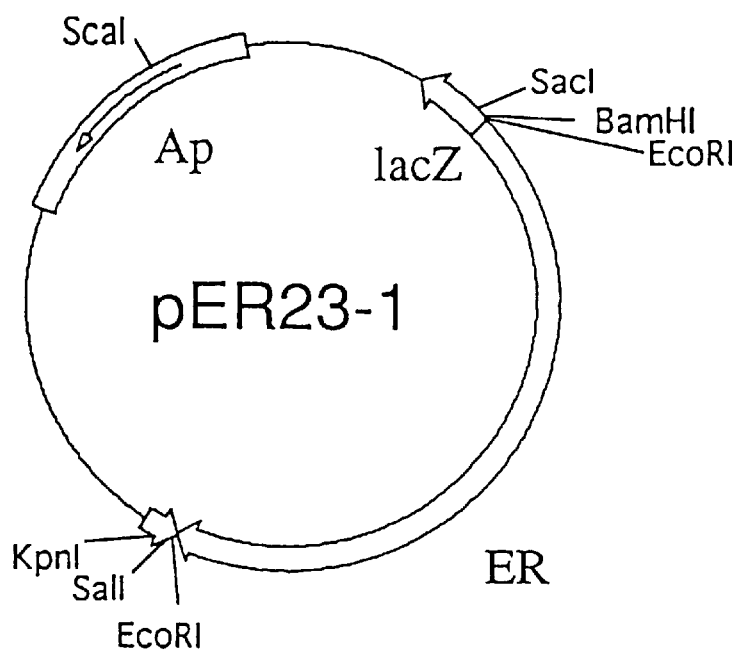
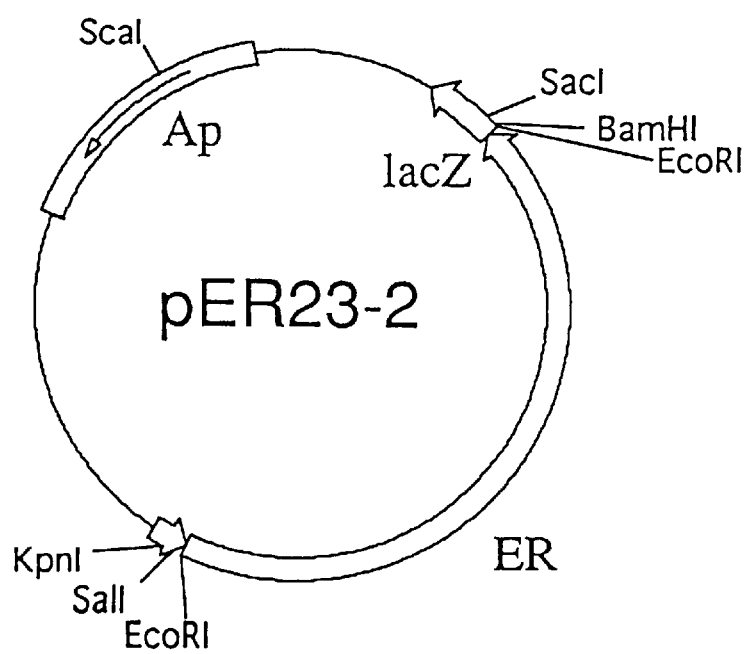

INHIBITION OF ELICITOR BINDING TO MEMBRANE FRACTION BY ANTIBODY

FIG. 9  RESISTANCE TO *P. nicotianae*

P: TOBACCO TRANSFORMED WITH pBI121 (CONTROL)

G: GLUCANASE-EXPRESSING TOBACCO

ER: ER-EXPRESSING TOBACCO

GxER: GLUCANASE/ER-COEXPRESSING TOBACCO

FIG. 10
RESISTANCE TO *R. solani*
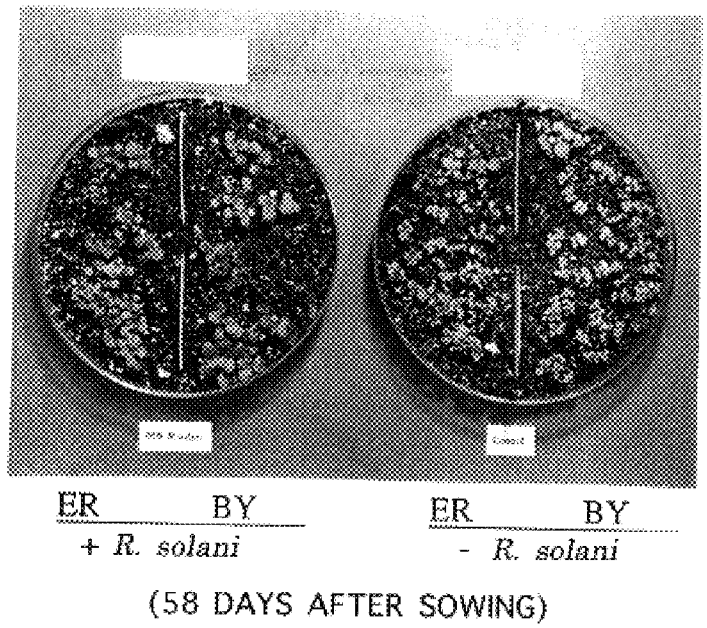
| ER | BY | ER | BY |
|---|---|---|---|
| + *R. solani* | | − *R. solani* | |
(58 DAYS AFTER SOWING)
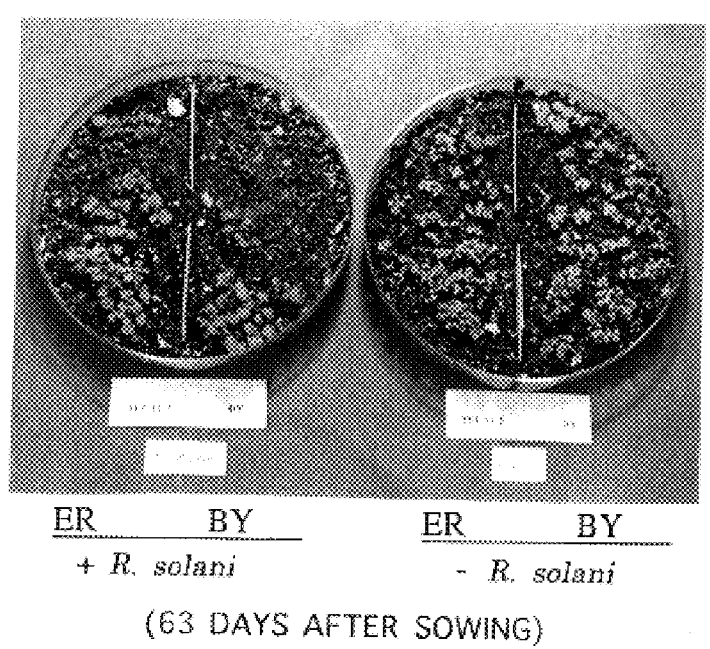
| ER | BY | ER | BY |
|---|---|---|---|
| + *R. solani* | | − *R. solani* | |
(63 DAYS AFTER SOWING)

BY-0: CONTROL TOBACCO
BY-0.5: CONTROL TOBACCO + *R. solani*
ER-0: ER-TRANSFORMED TOBACCO
ER-0.5: ER-TRANSFORMED TOBACCO + *R. solani*

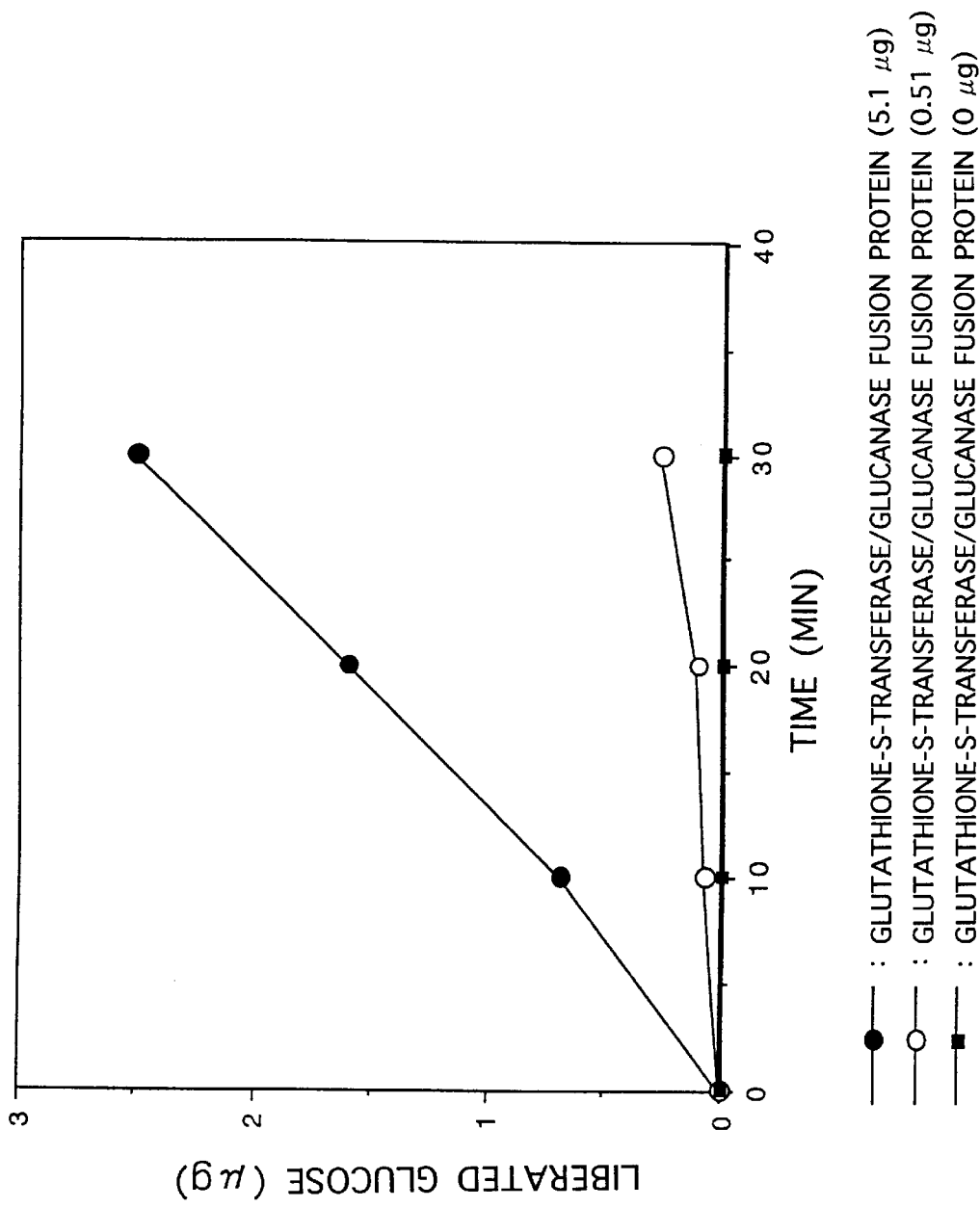
FIG. 14 ACTIVITY OF KIDNEY BEAN GLUCANASE

SEQUENCE LISTING (1) GENERAL INFORMATION:

(iii) NUMBER OF SEQUENCES: 36

(2) INFORMATION FOR SEQ ID NO: 1:

(i) SEQUENCE CHARACTERISTICS:
        (A) LENGTH: 667 amino acids
        (B) TYPE: amino acid
        (D) TOPOLOGY: linear (ii) MOLECULE TYPE: protein (xi) SEQUENCE DESCRIPTION: SEQ ID NO: 1:

Val Asn Ile Gln Thr Asn Thr Ser Tyr Ile Phe Pro Gln Thr Gln Ser
 1               5                  10                  15

-continued

```
Thr Val Leu Pro Asp Pro Ser Lys Phe Phe Ser Ser Asn Leu Leu Ser
             20                  25                  30

Ser Pro Leu Pro Thr Asn Ser Phe Phe Gln Asn Phe Val Leu Lys Asn
             35                  40                  45

Gly Asp Gln Gln Glu Tyr Ile His Pro Tyr Leu Ile Lys Ser Ser Asn
             50                  55                  60

Ser Ser Leu Ser Leu Ser Tyr Pro Ser Arg Gln Ala Ser Ser Ala Val
 65                  70                  75                  80

Ile Phe Gln Val Phe Asn Pro Asp Leu Thr Ile Ser Ala Pro Gln Gly
                 85                  90                  95

Pro Lys Gln Gly Pro Pro Gly Lys His Leu Ile Ser Ser Tyr Ser Asp
            100                 105                 110

Leu Ser Val Thr Leu Asp Phe Pro Ser Ser Asn Leu Ser Phe Phe Leu
            115                 120                 125

Val Arg Gly Ser Pro Tyr Leu Thr Val Ser Val Thr Gln Pro Thr Pro
            130                 135                 140

Leu Ser Ile Thr Thr Ile His Ser Ile Leu Ser Phe Ser Ser Asn Asp
145                 150                 155                 160

Ser Asn Thr Lys Tyr Thr Phe Gln Phe Asn Asn Gly Gln Thr Trp Leu
                165                 170                 175

Leu Tyr Ala Thr Ser Pro Ile Lys Leu Asn His Thr Leu Ser Glu Ile
                180                 185                 190

Thr Ser Asn Ala Phe Ser Gly Ile Ile Arg Ile Ala Leu Leu Pro Asp
            195                 200                 205

Ser Asp Ser Lys His Glu Ala Val Leu Asp Lys Tyr Ser Ser Cys Tyr
            210                 215                 220

Pro Val Ser Gly Lys Ala Val Phe Arg Glu Pro Phe Cys Val Glu Tyr
225                 230                 235                 240

Asn Trp Glu Lys Lys Asp Ser Gly Asp Leu Leu Leu Ala His Pro
                245                 250                 255

Leu His Val Gln Leu Leu Arg Asn Gly Asp Asn Asp Val Lys Ile Leu
            260                 265                 270

Glu Asp Leu Lys Tyr Lys Ser Ile Asp Gly Asp Leu Val Gly Val Val
            275                 280                 285

Gly Asp Ser Trp Val Leu Lys Thr Asp Pro Leu Phe Val Thr Trp His
290                 295                 300

Ser Ile Lys Gly Ile Lys Glu Glu Ser His Asp Glu Ile Val Ser Ala
305                 310                 315                 320

Leu Ser Lys Asp Val Glu Ser Leu Asp Ser Ser Ile Thr Thr Thr
                325                 330                 335

Glu Ser Tyr Phe Tyr Gly Lys Leu Ile Ala Arg Ala Ala Arg Leu Val
            340                 345                 350

Leu Ile Ala Glu Glu Leu Asn Tyr Pro Asp Val Ile Pro Lys Val Arg
            355                 360                 365

Asn Phe Leu Lys Glu Thr Ile Glu Pro Trp Leu Glu Gly Thr Phe Ser
            370                 375                 380

Gly Asn Gly Phe Leu His Asp Glu Lys Trp Gly Ile Ile Thr Gln
385                 390                 395                 400

Lys Gly Ser Thr Asp Ala Gly Gly Asp Phe Gly Phe Gly Ile Tyr Asn
                405                 410                 415

Asp His His Tyr His Leu Gly Tyr Phe Ile Tyr Gly Ile Ala Val Leu
            420                 425                 430
```

-continued

```
Thr Lys Leu Asp Pro Ala Trp Gly Arg Lys Tyr Lys Pro Gln Ala Tyr
        435                 440                 445

Ser Ile Val Gln Asp Phe Leu Asn Leu Asp Thr Lys Leu Asn Ser Asn
    450                 455                 460

Tyr Thr Arg Leu Arg Cys Phe Asp Pro Tyr Val Leu His Ser Trp Ala
465                 470                 475                 480

Gly Gly Leu Thr Glu Phe Thr Asp Gly Arg Asn Gln Glu Ser Thr Ser
                485                 490                 495

Glu Ala Val Ser Ala Tyr Tyr Ser Ala Leu Met Gly Leu Ala Tyr
            500                 505                 510

Gly Asp Ala Pro Leu Val Ala Leu Gly Ser Thr Leu Thr Ala Leu Glu
            515                 520                 525

Ile Glu Gly Thr Lys Met Trp Trp His Val Lys Glu Gly Gly Thr Leu
    530                 535                 540

Tyr Glu Lys Glu Phe Thr Gln Glu Asn Arg Val Met Gly Val Leu Trp
545                 550                 555                 560

Ser Asn Lys Arg Asp Thr Gly Leu Trp Phe Ala Pro Ala Glu Trp Lys
                565                 570                 575

Glu Cys Arg Leu Gly Ile Gln Leu Leu Pro Leu Ala Pro Ile Ser Glu
            580                 585                 590

Ala Ile Phe Ser Asn Val Asp Phe Val Lys Glu Leu Val Glu Trp Thr
        595                 600                 605

Leu Pro Ala Leu Asp Arg Glu Gly Val Gly Glu Gly Trp Lys Gly
    610                 615                 620

Phe Val Tyr Ala Leu Glu Gly Val Tyr Asp Asn Glu Ser Ala Leu Gln
625                 630                 635                 640

Lys Ile Arg Asn Leu Lys Gly Phe Asp Gly Asn Ser Leu Thr Asn
                645                 650                 655

Leu Leu Trp Trp Ile His Ser Arg Ser Asp Glu
                660                 665
```

(2) INFORMATION FOR SEQ ID NO: 2:

(i) SEQUENCE CHARACTERISTICS:
  (A) LENGTH: 2004 base pairs
  (B) TYPE: nucleic acid
  (C) STRANDEDNESS: double
  (D) TOPOLOGY: linear (ii) MOLECULE TYPE: cDNA (ix) FEATURE:
  (A) NAME/KEY: CDS
  (B) LOCATION: 1..2001

(xi) SEQUENCE DESCRIPTION: SEQ ID NO: 2:

```
GTT AAC ATC CAA ACC AAT ACA TCT TAC ATC TTC CCT CAA ACA CAA TCC      48
Val Asn Ile Gln Thr Asn Thr Ser Tyr Ile Phe Pro Gln Thr Gln Ser
 1               5                  10                  15

ACT GTT CTT CCT GAT CCC TCC AAA TTC TTC TCC TCA AAC CTT CTC TCA      96
Thr Val Leu Pro Asp Pro Ser Lys Phe Phe Ser Ser Asn Leu Leu Ser
            20                  25                  30

AGT CCA CTC CCC ACA AAC TCT TTC TTC CAA AAC TTT GTC CTA AAA AAT     144
Ser Pro Leu Pro Thr Asn Ser Phe Phe Gln Asn Phe Val Leu Lys Asn
        35                  40                  45

GGT GAC CAA CAA GAA TAC ATT CAT CCT TAC CTC ATC AAA TCC TCC AAC     192
Gly Asp Gln Gln Glu Tyr Ile His Pro Tyr Leu Ile Lys Ser Ser Asn
    50                  55                  60

TCT TCC CTC TCT CTC TCA TAC CCT TCT CGC CAA GCC AGT TCA GCT GTC     240
```

```
Ser Ser Leu Ser Leu Ser Tyr Pro Ser Arg Gln Ala Ser Ser Ala Val
 65                  70                  75                  80

ATA TTC CAA GTC TTC AAT CCT GAT CTT ACC ATT TCA GCC CCA CAA GGT        288
Ile Phe Gln Val Phe Asn Pro Asp Leu Thr Ile Ser Ala Pro Gln Gly
                 85                  90                  95

CCC AAA CAA GGT CCC CCT GGT AAA CAC CTT ATC TCC TCC TAC AGT GAT        336
Pro Lys Gln Gly Pro Pro Gly Lys His Leu Ile Ser Ser Tyr Ser Asp
            100                 105                 110

CTC AGT GTC ACC TTG GAT TTC CCT TCT TCC AAT CTG AGC TTC TTC CTT        384
Leu Ser Val Thr Leu Asp Phe Pro Ser Ser Asn Leu Ser Phe Phe Leu
        115                 120                 125

GTT AGG GGA AGC CCC TAT TTG ACT GTG TCT GTG ACT CAA CCA ACT CCT        432
Val Arg Gly Ser Pro Tyr Leu Thr Val Ser Val Thr Gln Pro Thr Pro
    130                 135                 140

CTT TCA ATT ACC ACC ATC CAT TCC ATT CTC TCA TTC TCT TCA AAT GAC        480
Leu Ser Ile Thr Thr Ile His Ser Ile Leu Ser Phe Ser Ser Asn Asp
145                 150                 155                 160

TCC AAC ACC AAG TAC ACC TTT CAG TTC AAC AAT GGT CAA ACA TGG CTT        528
Ser Asn Thr Lys Tyr Thr Phe Gln Phe Asn Asn Gly Gln Thr Trp Leu
                165                 170                 175

CTT TAT GCT ACC TCC CCC ATC AAG TTG AAC CAC ACC CTT TCT GAG ATA        576
Leu Tyr Ala Thr Ser Pro Ile Lys Leu Asn His Thr Leu Ser Glu Ile
            180                 185                 190

ACT TCT AAT GCA TTT TCT GGC ATA ATC CGG ATA GCT TTG TTG CCG GAT        624
Thr Ser Asn Ala Phe Ser Gly Ile Ile Arg Ile Ala Leu Leu Pro Asp
        195                 200                 205

TCG GAT TCG AAA CAC GAG GCT GTT CTT GAC AAG TAT AGT TCT TGT TAC        672
Ser Asp Ser Lys His Glu Ala Val Leu Asp Lys Tyr Ser Ser Cys Tyr
    210                 215                 220

CCC GTG TCA GGT AAA GCT GTG TTC AGA GAA CCT TTC TGT GTG GAA TAT        720
Pro Val Ser Gly Lys Ala Val Phe Arg Glu Pro Phe Cys Val Glu Tyr
225                 230                 235                 240

AAC TGG GAG AAG AAA GAT TCA GGG GAT TTG CTA CTC TTG GCT CAC CCT        768
Asn Trp Glu Lys Lys Asp Ser Gly Asp Leu Leu Leu Leu Ala His Pro
                245                 250                 255

CTC CAT GTT CAG CTT CTT CGT AAT GGA GAC AAT GAT GTC AAA ATT CTT        816
Leu His Val Gln Leu Leu Arg Asn Gly Asp Asn Asp Val Lys Ile Leu
            260                 265                 270

GAA GAT TTA AAG TAT AAA AGC ATT GAT GGG GAT CTT GTT GGT GTT GTC        864
Glu Asp Leu Lys Tyr Lys Ser Ile Asp Gly Asp Leu Val Gly Val Val
        275                 280                 285

GGG GAT TCA TGG GTT TTG AAA ACA GAT CCT TTG TTT GTA ACA TGG CAT        912
Gly Asp Ser Trp Val Leu Lys Thr Asp Pro Leu Phe Val Thr Trp His
    290                 295                 300

TCA ATC AAG GGA ATC AAA GAA GAA TCC CAT GAT GAG ATT GTC TCA GCC        960
Ser Ile Lys Gly Ile Lys Glu Glu Ser His Asp Glu Ile Val Ser Ala
305                 310                 315                 320

CTT TCT AAA GAT GTT GAG AGC CTA GAT TCA TCA TCA ATA ACT ACA ACA       1008
Leu Ser Lys Asp Val Glu Ser Leu Asp Ser Ser Ser Ile Thr Thr Thr
                325                 330                 335

GAG TCA TAT TTT TAT GGG AAG TTG ATT GCA AGG GCT GCA AGG TTG GTA       1056
Glu Ser Tyr Phe Tyr Gly Lys Leu Ile Ala Arg Ala Ala Arg Leu Val
            340                 345                 350

TTG ATT GCT GAG GAG TTG AAC TAC CCT GAT GTG ATT CCA AAG GTT AGG       1104
Leu Ile Ala Glu Glu Leu Asn Tyr Pro Asp Val Ile Pro Lys Val Arg
        355                 360                 365

AAT TTT TTG AAA GAA ACC ATT GAG CCA TGG TTG GAG GGA ACT TTT AGT       1152
Asn Phe Leu Lys Glu Thr Ile Glu Pro Trp Leu Glu Gly Thr Phe Ser
    370                 375                 380
```

```
GGG AAT GGA TTC CTA CAT GAT GAA AAA TGG GGT GGC ATT ATT ACC CAA     1200
Gly Asn Gly Phe Leu His Asp Glu Lys Trp Gly Gly Ile Ile Thr Gln
385                 390                 395                 400

AAG GGG TCC ACT GAT GCT GGT GGT GAT TTT GGA TTT GGA ATT TAC AAT     1248
Lys Gly Ser Thr Asp Ala Gly Gly Asp Phe Gly Phe Gly Ile Tyr Asn
                405                 410                 415

GAT CAC CAC TAT CAT TTG GGG TAC TTC ATT TAT GGA ATT GCG GTG CTC     1296
Asp His His Tyr His Leu Gly Tyr Phe Ile Tyr Gly Ile Ala Val Leu
            420                 425                 430

ACT AAG CTT GAT CCA GCA TGG GGT AGG AAG TAC AAG CCT CAA GCC TAT     1344
Thr Lys Leu Asp Pro Ala Trp Gly Arg Lys Tyr Lys Pro Gln Ala Tyr
        435                 440                 445

TCA ATA GTG CAA GAC TTC TTG AAC TTG GAC ACA AAA TTA AAC TCC AAT     1392
Ser Ile Val Gln Asp Phe Leu Asn Leu Asp Thr Lys Leu Asn Ser Asn
450                 455                 460

TAC ACA CGT TTG AGG TGT TTT GAC CCT TAT GTG CTT CAC TCT TGG GCT     1440
Tyr Thr Arg Leu Arg Cys Phe Asp Pro Tyr Val Leu His Ser Trp Ala
465                 470                 475                 480

GGA GGG TTA ACT GAG TTC ACA GAT GGA AGG AAT CAA GAG AGC ACA AGT     1488
Gly Gly Leu Thr Glu Phe Thr Asp Gly Arg Asn Gln Glu Ser Thr Ser
                485                 490                 495

GAG GCT GTG AGT GCA TAT TAT TCT GCT GCT TTG ATG GGA TTA GCA TAT     1536
Glu Ala Val Ser Ala Tyr Tyr Ser Ala Ala Leu Met Gly Leu Ala Tyr
            500                 505                 510

GGT GAT GCA CCT CTT GTT GCA CTT GGA TCA ACA CTC ACA GCA TTG GAA     1584
Gly Asp Ala Pro Leu Val Ala Leu Gly Ser Thr Leu Thr Ala Leu Glu
        515                 520                 525

ATT GAA GGG ACT AAA ATG TGG TGG CAT GTG AAA GAG GGA GGT ACT TTG     1632
Ile Glu Gly Thr Lys Met Trp Trp His Val Lys Glu Gly Gly Thr Leu
530                 535                 540

TAT GAG AAA GAG TTT ACA CAA GAG AAT AGG GTG ATG GGT GTT CTA TGG     1680
Tyr Glu Lys Glu Phe Thr Gln Glu Asn Arg Val Met Gly Val Leu Trp
545                 550                 555                 560

TCT AAC AAG AGG GAC ACT GGA CTT TGG TTT GCT CCT GCT GAG TGG AAA     1728
Ser Asn Lys Arg Asp Thr Gly Leu Trp Phe Ala Pro Ala Glu Trp Lys
                565                 570                 575

GAG TGT AGG CTT GGC ATT CAG CTC TTA CCA TTG GCT CCT ATT TCT GAA     1776
Glu Cys Arg Leu Gly Ile Gln Leu Leu Pro Leu Ala Pro Ile Ser Glu
            580                 585                 590

GCC ATT TTC TCC AAT GTT GAC TTT GTA AAG GAG CTT GTG GAG TGG ACT     1824
Ala Ile Phe Ser Asn Val Asp Phe Val Lys Glu Leu Val Glu Trp Thr
        595                 600                 605

TTG CCT GCT TTG GAT AGG GAG GGT GGT GTT GGT GAA GGA TGG AAG GGG     1872
Leu Pro Ala Leu Asp Arg Glu Gly Gly Val Gly Glu Gly Trp Lys Gly
610                 615                 620

TTT GTG TAT GCC CTT GAA GGG GTT TAT GAC AAT GAA AGT GCA CTG CAG     1920
Phe Val Tyr Ala Leu Glu Gly Val Tyr Asp Asn Glu Ser Ala Leu Gln
625                 630                 635                 640

AAG ATA AGA AAC CTG AAA GGT TTT GAT GGT GGA AAC TCT TTG ACC AAT     1968
Lys Ile Arg Asn Leu Lys Gly Phe Asp Gly Gly Asn Ser Leu Thr Asn
                645                 650                 655

CTC TTG TGG TGG ATT CAT AGC AGA AGT GAT GAA TAG                     2004
Leu Leu Trp Trp Ile His Ser Arg Ser Asp Glu
            660                 665
```

(2) INFORMATION FOR SEQ ID NO: 3:

(i) SEQUENCE CHARACTERISTICS:
        (A) LENGTH: 347 amino acids
        (B) TYPE: amino acid
        (D) TOPOLOGY: linear (ii) MOLECULE TYPE: protein (xi) SEQUENCE DESCRIPTION: SEQ ID NO: 3:

| Met | Ala | Lys | Tyr | His | Ser | Ser | Gly | Lys | Ser | Ser | Ile | Thr | Ala | Ile |
|---|---|---|---|---|---|---|---|---|---|---|---|---|---|---|
| 1 | | | | 5 | | | | | 10 | | | | | 15 |

| Ala | Phe | Leu | Phe | Ile | Leu | Leu | Ile | Thr | Tyr | Thr | Gly | Thr | Thr | Asp | Ala |
|---|---|---|---|---|---|---|---|---|---|---|---|---|---|---|---|
| | | | 20 | | | | | 25 | | | | | 30 | | |

| Gln | Ser | Gly | Val | Cys | Tyr | Gly | Arg | Leu | Gly | Asn | Asn | Leu | Pro | Thr | Pro |
|---|---|---|---|---|---|---|---|---|---|---|---|---|---|---|---|
| | | 35 | | | | | 40 | | | | | 45 | | | |

| Gln | Glu | Val | Val | Ala | Leu | Tyr | Asn | Gln | Ala | Asn | Ile | Arg | Arg | Met | Arg |
|---|---|---|---|---|---|---|---|---|---|---|---|---|---|---|---|
| | 50 | | | | | 55 | | | | | 60 | | | | |

| Ile | Tyr | Gly | Pro | Ser | Pro | Glu | Val | Leu | Glu | Ala | Leu | Arg | Gly | Ser | Asn |
|---|---|---|---|---|---|---|---|---|---|---|---|---|---|---|---|
| 65 | | | | | 70 | | | | | 75 | | | | | 80 |

| Ile | Glu | Leu | Leu | Leu | Asp | Ile | Pro | Asn | Asp | Asn | Leu | Arg | Asn | Leu | Ala |
|---|---|---|---|---|---|---|---|---|---|---|---|---|---|---|---|
| | | | | 85 | | | | | 90 | | | | | 95 | |

| Ser | Ser | Gln | Asp | Asn | Ala | Asn | Lys | Trp | Val | Gln | Asp | Asn | Ile | Lys | Asn |
|---|---|---|---|---|---|---|---|---|---|---|---|---|---|---|---|
| | | | | 100 | | | | | 105 | | | | | 110 | |

| Tyr | Ala | Asn | Asn | Val | Arg | Phe | Arg | Tyr | Val | Ser | Val | Gly | Asn | Glu | Val |
|---|---|---|---|---|---|---|---|---|---|---|---|---|---|---|---|
| | | 115 | | | | | 120 | | | | | 125 | | | |

| Lys | Pro | Glu | His | Ser | Phe | Ala | Gln | Phe | Leu | Val | Pro | Ala | Leu | Glu | Asn |
|---|---|---|---|---|---|---|---|---|---|---|---|---|---|---|---|
| | 130 | | | | | 135 | | | | | 140 | | | | |

| Ile | Gln | Arg | Ala | Ile | Ser | Asn | Ala | Gly | Leu | Gly | Asn | Gln | Val | Lys | Val |
|---|---|---|---|---|---|---|---|---|---|---|---|---|---|---|---|
| 145 | | | | | 150 | | | | | 155 | | | | | 160 |

| Ser | Thr | Ala | Ile | Asp | Thr | Gly | Ala | Leu | Ala | Glu | Ser | Phe | Pro | Pro | Ser |
|---|---|---|---|---|---|---|---|---|---|---|---|---|---|---|---|
| | | | | 165 | | | | | 170 | | | | | 175 | |

| Lys | Gly | Ser | Phe | Lys | Ser | Asp | Tyr | Arg | Gly | Ala | Tyr | Leu | Asp | Gly | Val |
|---|---|---|---|---|---|---|---|---|---|---|---|---|---|---|---|
| | | | 180 | | | | | 185 | | | | | 190 | | |

| Ile | Arg | Phe | Leu | Val | Asn | Asn | Ala | Pro | Leu | Met | Val | Asn | Val | Tyr |
|---|---|---|---|---|---|---|---|---|---|---|---|---|---|---|
| | | 195 | | | | | 200 | | | | | 205 | | |

| Ser | Tyr | Phe | Ala | Tyr | Thr | Ala | Asn | Pro | Lys | Asp | Ile | Ser | Leu | Asp | Tyr |
|---|---|---|---|---|---|---|---|---|---|---|---|---|---|---|---|
| | 210 | | | | | 215 | | | | | 220 | | | | |

| Ala | Leu | Phe | Arg | Ser | Pro | Ser | Val | Val | Gln | Asp | Gly | Ser | Leu | Gly |
|---|---|---|---|---|---|---|---|---|---|---|---|---|---|---|
| 225 | | | | | 230 | | | | | 235 | | | | 240 |

| Tyr | Arg | Asn | Leu | Phe | Asp | Ala | Ser | Val | Asp | Ala | Val | Tyr | Ala | Ala | Leu |
|---|---|---|---|---|---|---|---|---|---|---|---|---|---|---|---|
| | | | | 245 | | | | | 250 | | | | | 255 | |

| Glu | Lys | Ala | Gly | Gly | Gly | Ser | Leu | Asn | Ile | Val | Val | Ser | Glu | Ser | Gly |
|---|---|---|---|---|---|---|---|---|---|---|---|---|---|---|---|
| | | 260 | | | | | 265 | | | | | 270 | | | |

| Trp | Pro | Ser | Ser | Gly | Gly | Thr | Ala | Thr | Ser | Leu | Asp | Asn | Ala | Arg | Thr |
|---|---|---|---|---|---|---|---|---|---|---|---|---|---|---|---|
| | | 275 | | | | | 280 | | | | | 285 | | | |

| Tyr | Asn | Thr | Asn | Leu | Val | Arg | Asn | Val | Lys | Gln | Gly | Thr | Pro | Lys | Arg |
|---|---|---|---|---|---|---|---|---|---|---|---|---|---|---|---|
| | 290 | | | | | 295 | | | | | 300 | | | | |

| Pro | Gly | Ala | Pro | Leu | Glu | Thr | Tyr | Val | Phe | Ala | Met | Phe | Asp | Glu | Asn |
|---|---|---|---|---|---|---|---|---|---|---|---|---|---|---|---|
| 305 | | | | | 310 | | | | | 315 | | | | | 320 |

| Gln | Lys | Gln | Pro | Glu | Phe | Glu | Lys | Phe | Trp | Gly | Leu | Phe | Ser | Pro | Ile |
|---|---|---|---|---|---|---|---|---|---|---|---|---|---|---|---|
| | | | | 325 | | | | | 330 | | | | | 335 | |

| Thr | Lys | Gln | Pro | Lys | Tyr | Ser | Ile | Asn | Phe | Asn |
|---|---|---|---|---|---|---|---|---|---|---|
| | | | 340 | | | | | 345 | | |

(2) INFORMATION FOR SEQ ID NO: 4:

(i) SEQUENCE CHARACTERISTICS:
  (A) LENGTH: 1044 base pairs
  (B) TYPE: nucleic acid
  (C) STRANDEDNESS: double
  (D) TOPOLOGY: linear (ii) MOLECULE TYPE: cDNA (ix) FEATURE:
    (A) NAME/KEY: CDS
    (B) LOCATION: 1..1041

(xi) SEQUENCE DESCRIPTION: SEQ ID NO: 4:

```
ATG GCT AAG TAT CAT TCA AGT GGG AAA AGC TCT TCC ATC ACT GCT ATA      48
Met Ala Lys Tyr His Ser Ser Gly Lys Ser Ser Ser Ile Thr Ala Ile
 1               5                  10                  15

GCC TTC CTG TTT ATC CTT CTA ATC ACT TAT ACA GGC ACA ACA GAT GCA      96
Ala Phe Leu Phe Ile Leu Leu Ile Thr Tyr Thr Gly Thr Thr Asp Ala
                20                  25                  30

CAA TCC GGG GTA TGT TAT GGA AGA CTT GGC AAC AAC TTA CCA ACC CCT     144
Gln Ser Gly Val Cys Tyr Gly Arg Leu Gly Asn Asn Leu Pro Thr Pro
             35                  40                  45

CAA GAA GTT GTG GCC CTC TAC AAT CAA GCC AAC ATT CGC AGG ATG CGA     192
Gln Glu Val Val Ala Leu Tyr Asn Gln Ala Asn Ile Arg Arg Met Arg
         50                  55                  60

ATC TAC GGT CCA AGC CCA GAA GTC CTC GAA GCA CTA AGA GGT TCC AAC     240
Ile Tyr Gly Pro Ser Pro Glu Val Leu Glu Ala Leu Arg Gly Ser Asn
 65                  70                  75                  80

ATT GAG CTT TTG CTA GAC ATT CCA AAT GAC AAC CTC AGA AAC CTA GCA     288
Ile Glu Leu Leu Leu Asp Ile Pro Asn Asp Asn Leu Arg Asn Leu Ala
                 85                  90                  95

TCT AGC CAA GAC AAT GCA AAC AAA TGG GTG CAA GAC AAC ATC AAA AAC     336
Ser Ser Gln Asp Asn Ala Asn Lys Trp Val Gln Asp Asn Ile Lys Asn
                100                 105                 110

TAT GCC AAC AAT GTC AGA TTC AGA TAC GTT TCA GTG GGA AAT GAA GTG     384
Tyr Ala Asn Asn Val Arg Phe Arg Tyr Val Ser Val Gly Asn Glu Val
            115                 120                 125

AAA CCC GAA CAC TCA TTT GCA CAA TTT CTA GTG CCT GCA TTG GAA AAC     432
Lys Pro Glu His Ser Phe Ala Gln Phe Leu Val Pro Ala Leu Glu Asn
        130                 135                 140

ATT CAG AGG GCC ATT TCT AAT GCT GGC CTT GGA AAC CAA GTA AAA GTT     480
Ile Gln Arg Ala Ile Ser Asn Ala Gly Leu Gly Asn Gln Val Lys Val
145                 150                 155                 160

TCC ACT GCC ATT GAT ACT GGT GCC TTG GCA GAA TCA TTC CCA CCA TCA     528
Ser Thr Ala Ile Asp Thr Gly Ala Leu Ala Glu Ser Phe Pro Pro Ser
                165                 170                 175

AAG GGT TCC TTC AAA TCT GAT TAT AGA GGA GCA TAT CTT GAT GGT GTC     576
Lys Gly Ser Phe Lys Ser Asp Tyr Arg Gly Ala Tyr Leu Asp Gly Val
            180                 185                 190

ATC AGA TTT CTA GTG AAC AAT AAT GCC CCA TTA ATG GTT AAT GTG TAC     624
Ile Arg Phe Leu Val Asn Asn Asn Ala Pro Leu Met Val Asn Val Tyr
        195                 200                 205

TCT TAC TTC GCT TAC ACT GCA AAC CCT AAG GAC ATT AGT CTT GAC TAT     672
Ser Tyr Phe Ala Tyr Thr Ala Asn Pro Lys Asp Ile Ser Leu Asp Tyr
    210                 215                 220

GCA CTT TTT AGG TCT CCT TCG GTG GTA GTG CAA GAT GGT TCA CTT GGT     720
Ala Leu Phe Arg Ser Pro Ser Val Val Val Gln Asp Gly Ser Leu Gly
225                 230                 235                 240

TAC CGT AAC CTC TTT GAT GCT TCG GTT GAT GCT GTT TAT GCT GCA TTG     768
Tyr Arg Asn Leu Phe Asp Ala Ser Val Asp Ala Val Tyr Ala Ala Leu
                245                 250                 255

GAG AAA GCA GGA GGA GGG TCA TTG AAC ATA GTT GTG TCT GAG AGT GGA     816
Glu Lys Ala Gly Gly Gly Ser Leu Asn Ile Val Val Ser Glu Ser Gly
            260                 265                 270

TGG CCT TCT TCT GGT GGA ACT GCA ACT TCA CTT GAT AAT GCA AGA ACT     864
Trp Pro Ser Ser Gly Gly Thr Ala Thr Ser Leu Asp Asn Ala Arg Thr
```

```
             275                 280                       285
TAC AAC ACA AAC TTG GTT CGG AAT GTG AAG CAA GGA ACC CCT AAA AGG        912
Tyr Asn Thr Asn Leu Val Arg Asn Val Lys Gln Gly Thr Pro Lys Arg
    290                 295                 300

CCT GGT GCA CCC CTT GAA ACT TAT GTG TTT GCC ATG TTT GAT GAA AAT        960
Pro Gly Ala Pro Leu Glu Thr Tyr Val Phe Ala Met Phe Asp Glu Asn
305                 310                 315                 320

CAG AAG CAG CCA GAG TTT GAA AAA TTT TGG GGG CTC TTT TCT CCT ATA       1008
Gln Lys Gln Pro Glu Phe Glu Lys Phe Trp Gly Leu Phe Ser Pro Ile
                325                 330                 335

ACT AAG CAG CCC AAA TAC TCG ATT AAT TTC AAT TAA                       1044
Thr Lys Gln Pro Lys Tyr Ser Ile Asn Phe Asn
            340                 345
```

(2) INFORMATION FOR SEQ ID NO: 5:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 5:

```
Val Asn Ile Gln Thr Asn Thr Ser Asn Ile Ser Pro Gln
1               5                   10
```

(2) INFORMATION FOR SEQ ID NO: 6:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 6:

```
Lys Ser Ile Asp Gly Asp Leu Val Gly Val Val Gly Asp Ser
1               5                   10
```

(2) INFORMATION FOR SEQ ID NO: 7:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 7:

```
Lys Tyr Lys Pro Gln Ala Tyr Ser Ile Val Gln Asp Phe Leu Asn Leu
1               5                   10                  15
Asp
```

(2) INFORMATION FOR SEQ ID NO: 8:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 8:

Lys Thr Asp Pro Leu Phe Val Thr Trp His Ser Ile Lys
1               5                   10

(2) INFORMATION FOR SEQ ID NO: 9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

AARAGYATHG AYGGNGA                                                      17

(2) INFORMATION FOR SEQ ID NO: 10:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 10:

WRTCNCCNAC NAC                                                          13

(2) INFORMATION FOR SEQ ID NO: 11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 11:

GTNAAYAARA TNCARAC                                                      17

(2) INFORMATION FOR SEQ ID NO: 12:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 12:

ARRTTNAGRA ARTCYTC                                                      17

(2) INFORMATION FOR SEQ ID NO: 13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 13:

AAGTAYAAGC CRCAAGCCTA TTCA                                              24

(2) INFORMATION FOR SEQ ID NO: 14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 14:

ATCGCCRACA ACMCCAA                                                  17

(2) INFORMATION FOR SEQ ID NO: 15:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 15:

GGAATTCGAG CTCGGTACCC GGGGGATCCT CTAGAGTCGA CCTGCAGGCA TGCA       54

(2) INFORMATION FOR SEQ ID NO: 16:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 16:

CCTTAAGCTC GAGCCATGGG CCCCCTAGGA GATCTCAGCT GGACGTCCGT ACGTTCGA       58

(2) INFORMATION FOR SEQ ID NO: 17:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 17:

ATGGATCCAT GGTTAACATC CAAACC                                   26

(2) INFORMATION FOR SEQ ID NO: 18:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 18:

ATGGATCCGA ATATAACTGG GAGAAG                                   26

(2) INFORMATION FOR SEQ ID NO: 19:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO: 19:

ATGGATCCCC AGCATGGGGT AGGAAG                        26

(2) INFORMATION FOR SEQ ID NO: 20:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 20:

TAGTCGACTA CTTCTCCCAG TTATATTC                     28

(2) INFORMATION FOR SEQ ID NO: 21:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 21:

TAGTCGACTA CTTCCTACCC CATGCTGG                     28

(2) INFORMATION FOR SEQ ID NO: 22:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 22:

TAGTCGACTA TTCATCACTT CTGCTATG                     28

(2) INFORMATION FOR SEQ ID NO: 23:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 23:

ATGGATCCGC CCCACAAGGT CCCAAA                        26

(2) INFORMATION FOR SEQ ID NO: 24:

(i) SEQUENCE CHARACTERISTICS:
        (A) LENGTH: 26 base pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ ID NO: 24:

ATGGATCCAA TGACTCCAAC ACCAAG                                        26

(2) INFORMATION FOR SEQ ID NO: 25:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 25:

ATGGATCCGA ATATAACTGG GAGAAG                                        26

(2) INFORMATION FOR SEQ ID NO: 26:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 26:

TAGTCGACTA CTTCCTACCC CATGCTGG                                      28

(2) INFORMATION FOR SEQ ID NO: 27:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 27:

CTAGAGGATC CGGTACCCCC GGGGTCGACG AGCT                               34

(2) INFORMATION FOR SEQ ID NO: 28:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 28:

CGTCGACCCC GGGGGTACCG GATCCT                                        26

(2) INFORMATION FOR SEQ ID NO: 29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 29:

CACCTTCAGC AACAATGGTT                                                      20

(2) INFORMATION FOR SEQ ID NO: 30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 30:

CTATTCATCA CTTCTGCTAT                                                      20

(2) INFORMATION FOR SEQ ID NO: 31:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 31:

CAAATGTTGT GGTGAGGGAT GGCC                                                 24

(2) INFORMATION FOR SEQ ID NO: 32:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 32:

AAATGTTTCT CTATCTCAGG ACTC                                                 24

(2) INFORMATION FOR SEQ ID NO: 33:

(i) SEQUENCE CHARACTERISTICS:
        (A) LENGTH: 996 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..993

(xi) SEQUENCE DESCRIPTION: SEQ ID NO: 33:

```
ATG TCT GCC TTA TTG CTG CTT CTT GGA GTA TTA TCT TCC ACT GGA GTA        48
Met Ser Ala Leu Leu Leu Leu Leu Gly Val Leu Ser Ser Thr Gly Val
 1               5                  10                  15

CTG CTT ACT GGG GTA GAA TCT GTG GGT GTG TGT TAT GGA GGA AAT GGA        96
Leu Leu Thr Gly Val Glu Ser Val Gly Val Cys Tyr Gly Gly Asn Gly
                20                  25                  30

AAC AAT CTA CCA ACA AAG CAA GCA GTG GTG AAT CTC TAC AAA TCA AAC       144
Asn Asn Leu Pro Thr Lys Gln Ala Val Val Asn Leu Tyr Lys Ser Asn
            35                  40                  45

GGA ATT GGC AAA ATC CGT TTA TAC TAT CCA GAT GAA GGT GCC CTT CAA       192
```

```
Gly Ile Gly Lys Ile Arg Leu Tyr Tyr Pro Asp Glu Gly Ala Leu Gln
         50                  55                  60

GCC CTC AGA GGT TCA AAC ATA GAA GTG ATA CTT GCT GTT CCT AAT GAT      240
Ala Leu Arg Gly Ser Asn Ile Glu Val Ile Leu Ala Val Pro Asn Asp
 65                  70                  75                  80

CAA CTT CAA TCT GTC TCC AAC AAT GGA GGT GCA ACA AAT TGG GTC AAC      288
Gln Leu Gln Ser Val Ser Asn Asn Gly Gly Ala Thr Asn Trp Val Asn
                     85                  90                  95

AAG TAC GTG AAA CCC TAT GCA GGA AAC GTG AAA TTG AAG TAC ATT GCA      336
Lys Tyr Val Lys Pro Tyr Ala Gly Asn Val Lys Leu Lys Tyr Ile Ala
                100                 105                 110

GTT GGC AAC GAA GTT CAC CCT GGT GAT GCT CTA GCA GGC TCA GTT CTT      384
Val Gly Asn Glu Val His Pro Gly Asp Ala Leu Ala Gly Ser Val Leu
            115                 120                 125

CCA GCA CTT CAA AGC ATT CAG AAC GCA ATT TCT GCA GCA AAT TTG CAA      432
Pro Ala Leu Gln Ser Ile Gln Asn Ala Ile Ser Ala Ala Asn Leu Gln
130                 135                 140

CGC CAA ATC AAA GTC TCC ACA GCA ATA GAC ACC ACT CTA CTG GGC AAC      480
Arg Gln Ile Lys Val Ser Thr Ala Ile Asp Thr Thr Leu Leu Gly Asn
145                 150                 155                 160

TCT TAC CCA CCA AAA GAT GGC GTT TTC AGC AAC AGT GCA AGT TCA TAC      528
Ser Tyr Pro Pro Lys Asp Gly Val Phe Ser Asn Ser Ala Ser Ser Tyr
                165                 170                 175

ATA ACT CCA ATC ATA AAC TTT TTA GCC AAA AAC GGT GCC CCA CTT CTT      576
Ile Thr Pro Ile Ile Asn Phe Leu Ala Lys Asn Gly Ala Pro Leu Leu
                180                 185                 190

GCA AAC GTG TAC CCT TAC TTC GCC TAC GTT AAC AAT CAA CAA AAC ATT      624
Ala Asn Val Tyr Pro Tyr Phe Ala Tyr Val Asn Asn Gln Gln Asn Ile
            195                 200                 205

GGT CTT GAT TAT GCC TTG TTT ACC AAA CAA GGC AAC AAC GAA GTT GGG      672
Gly Leu Asp Tyr Ala Leu Phe Thr Lys Gln Gly Asn Asn Glu Val Gly
210                 215                 220

TAC CAA AAC CTG TTT GAT GCA TTG GTG GAT TCT CTG TAC GCA GCT CTT      720
Tyr Gln Asn Leu Phe Asp Ala Leu Val Asp Ser Leu Tyr Ala Ala Leu
225                 230                 235                 240

GAG AAA GTG GGA GCA TCA AAT GTG AAG GTT GTT GTG TCT GAG AGT GGG      768
Glu Lys Val Gly Ala Ser Asn Val Lys Val Val Val Ser Glu Ser Gly
                245                 250                 255

TGG CCA TCA CAA GGT GGA GTT GGA GCC ACT GTT CAA AAC GCA GGA ACG      816
Trp Pro Ser Gln Gly Gly Val Gly Ala Thr Val Gln Asn Ala Gly Thr
                260                 265                 270

TAT TAC AGG AAT TTG ATC AAA CAT GTT AAG GGT GGC ACC CCA AAG AGG      864
Tyr Tyr Arg Asn Leu Ile Lys His Val Lys Gly Gly Thr Pro Lys Arg
            275                 280                 285

CCT AAT GGA CCC ATA GAG ACT TAC CTC TTT GCC ATG TTT GAT GAA AAC      912
Pro Asn Gly Pro Ile Glu Thr Tyr Leu Phe Ala Met Phe Asp Glu Asn
290                 295                 300

CAG AAG GGT GGT GCA GAA ACT GAG AAA CAC TTT GGT CTC TTC AGG CCT      960
Gln Lys Gly Gly Ala Glu Thr Glu Lys His Phe Gly Leu Phe Arg Pro
305                 310                 315                 320

GAT AAA TCA CCA AAA TAC CAA CTC AGT TTC AAT TGA                      996
Asp Lys Ser Pro Lys Tyr Gln Leu Ser Phe Asn
                325                 330

(2) INFORMATION FOR SEQ ID NO: 34:

(i) SEQUENCE CHARACTERISTICS:
        (A) LENGTH: 331 amino acids
        (B) TYPE: amino acid
        (D) TOPOLOGY: linear
```

(ii) MOLECULE TYPE: protein (xi) SEQUENCE DESCRIPTION: SEQ ID NO: 34:

```
Met Ser Ala Leu Leu Leu Leu Gly Val Leu Ser Ser Thr Gly Val
 1               5                  10                  15

Leu Leu Thr Gly Val Glu Ser Val Gly Val Cys Tyr Gly Asn Gly
                20                  25                  30

Asn Asn Leu Pro Thr Lys Gln Ala Val Val Asn Leu Tyr Lys Ser Asn
            35                  40                  45

Gly Ile Gly Lys Ile Arg Leu Tyr Tyr Pro Asp Glu Gly Ala Leu Gln
 50                      55                  60

Ala Leu Arg Gly Ser Asn Ile Glu Val Ile Leu Ala Val Pro Asn Asp
 65                  70                      75                  80

Gln Leu Gln Ser Val Ser Asn Gly Gly Ala Thr Asn Trp Val Asn
                85                  90                  95

Lys Tyr Val Lys Pro Tyr Ala Gly Asn Val Lys Leu Lys Tyr Ile Ala
                100                 105                 110

Val Gly Asn Glu Val His Pro Gly Asp Ala Leu Ala Gly Ser Val Leu
            115                 120                 125

Pro Ala Leu Gln Ser Ile Gln Asn Ala Ile Ser Ala Ala Asn Leu Gln
130                 135                     140

Arg Gln Ile Lys Val Ser Thr Ala Ile Asp Thr Thr Leu Leu Gly Asn
145                 150                 155                 160

Ser Tyr Pro Pro Lys Asp Gly Val Phe Ser Asn Ser Ala Ser Ser Tyr
                165                 170                 175

Ile Thr Pro Ile Ile Asn Phe Leu Ala Lys Asn Gly Ala Pro Leu Leu
            180                 185                 190

Ala Asn Val Tyr Pro Tyr Phe Ala Tyr Val Asn Asn Gln Gln Asn Ile
            195                 200                 205

Gly Leu Asp Tyr Ala Leu Phe Thr Lys Gln Gly Asn Asn Glu Val Gly
        210                 215                 220

Tyr Gln Asn Leu Phe Asp Ala Leu Val Asp Ser Leu Tyr Ala Ala Leu
225                 230                     235                 240

Glu Lys Val Gly Ala Ser Asn Val Lys Val Val Ser Glu Ser Gly
                245                 250                 255

Trp Pro Ser Gln Gly Gly Val Gly Ala Thr Val Gln Asn Ala Gly Thr
                260                 265                 270

Tyr Tyr Arg Asn Leu Ile Lys His Val Lys Gly Thr Pro Lys Arg
        275                 280                 285

Pro Asn Gly Pro Ile Glu Thr Tyr Leu Phe Ala Met Phe Asp Glu Asn
        290                 295                 300

Gln Lys Gly Gly Ala Glu Thr Glu Lys His Phe Gly Leu Phe Arg Pro
305                 310                 315                 320

Asp Lys Ser Pro Lys Tyr Gln Leu Ser Phe Asn
                325                 330
```

(2) INFORMATION FOR SEQ ID NO: 35:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO: 35:

```
GGAATTCCGA ATCTGTGGGT GTGTGTTAT                                         29

(2) INFORMATION FOR SEQ ID NO: 36:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 36:

GGAAACAGCT ATGACCATGA TTAGC                                             25
```

GLUCAN ELICITOR RECEPTOR, DNA MOLECULE CODING THEREFOR, FUNGUS-RESISTANT PLANTS TRANSFORMED WITH THE DNA MOLECULE AND METHOD FOR CREATING THE PLANTS

CROSS-REFERENCE TO RELATED APPLICATIONS

This application is a continuation-in-part application of U.S. application Ser. No. 08/591,566 now abandoned filed Jul. 14, 1997 and of PCT/JP96/03653 filed Dec. 15, 1996.

BACKGROUND OF THE INVENTION

The present invention relates to a glucan elicitor receptor, DNA molecules coding for the glucan elicitor receptor, vectors containing the DNA molecules, plant cells transformed with the DNA molecules, fungus-resistant plants transformed with the DNA molecules and a method for creating such plants. More specifically, the present invention relates to a glucan elicitor receptor derived from a soybean root plasma membrane fraction, DNA molecules coding for the glucan elicitor receptor, vectors containing the DNA molecules, plant cells transformed with the DNA molecules, fungus-resistant plants transformed with the DNA molecules and a method for creating such plants.

It is known that plants synthesize and accumulate an antibiotic agent called phytoalexin in response to infection with pathogens (M. Yoshikawa (1978) Nature 257: 546). Some plant pathogens were found to have the substances that induce them to perform such a resistance reaction (N. T. Keen (1975) Science 187: 74), which are called "elicitors". The biochemical process from the infection of plants with pathogens to the synthesis and accumulation of phytoalexin is believed to be as follows:

When the mycelium of a pathogen invades a plant cell, glucanase in the plant cell works so as to cleave polysaccharides on the surface of the pathogen mycelial wall, thereby liberating an elicitor. If the elicitor binds to a receptor in the plant cell, a second messenger which plays a role in signal transduction is produced. The signal transduction substance is incorporated in the nucleus of the plant cell and activates the transcription of the genes coding for phytoalexin synthesize enzymes to induce a phytoalexin synthesis. At the same time, the phytoalexin degradation is inhibited. As a result, phytoalexin is efficiently accumulated in the plant cell.

A phytoalexin playing an important role in the resistance of soybean is called glyceollin and its structure has been determined (M. Yoshikawa et al. (1978) Physiol. Plant. Pathol. 12: 73). Elicitor of soybean has a characteristic structure; it has β-1,6 linked glucan of various lengths as a principal chain from which β-1,3 linked glucan side chains are branched [J. K. Sharp et al. (1984) J. Biol. Chem. 259: 11321; M. Yoshikawa (1990) Plant Cell Technology 1.2: 695]. A receptor specific for a glucan elicitor derived from a soybean pathogenic mold fungus *Phytophthora megasperma* f. sp. *glycinea* is believed to be a protein which plays an important role in the synthesis and accumulation of the antibiotic agent glyceollin. A method for the purification of the glucan elicitor receptor specific to this elicitor has been disclosed (E. G. Cosio et al., (1990) FEBS 264: 235, E. G. Cosio et al. (1992) Eur. J. Biochem. 204: 1115, T. Frey et al. (1993) Phytochemistry 32; 543). However, the amino acid sequence of a glucan elicitor receptor has not been determined and the gene coding therefor is not yet known. If a gene coding for glucan elicitor receptor is found, it will be possible to create plants having resistance to pathogenic fungi by incorporating the gene into a chromosome of plants and expressing the glucan elicitor receptor in the plants. Thus, improvement of the productivity of agricultural products can be expected.

An object of the present invention is to provide a glucan elictor receptor.

Another object of the present invention is to provide a DNA molecule coding for a glucan elicitor receptor.

A further object of the present invention is to provide a vector containing a DNA molecule coding for a glucan elicitor receptor.

A still further object of the present invention is to provide a plant cell transformed with a DNA molecule coding for a glucan elicitor receptor.

It is an object of the present invention to provide a plant transformed with a DNA molecule coding for a glucan elicitor receptor.

It is another object of the present invention to provide a method for creating a plant transformed with a DNA molecule coding for a glucan elicitor receptor.

SUMMARY OF THE INVENTION

As a result of intensive and extensive researches toward the resolution of the above assignment, the present inventors have succeeded in purifying a soybean root-derived glucan elicitor receptor, cloning a glucan elicitor receptor gene from a soybean cDNA library, transferring this gene into a tobacco plant and expressing it in the plant. Thus, the present invention has been achieved. The present invention provides a glucan elicitor receptor having an amino acid sequence as substantially shown in SEQ ID NO:1. The present invention also provides DNA molecules containing nucleotide sequences coding for a glucan elicitor receptor having an amino acid sequence as substantially shown in SEQ ID NO:1, and fragments thereof. The present invention further provides DNA molecules containing nucleotide sequences coding for a glucan elicitor receptor which are incorporated in plasmid pER23-1, and fragments thereof. The present invention still further provides vectors containing DNA molecules coding for a glucan elicitor receptor and plant cells transformed with DNA molecules coding for a glucan elicitor receptor. Moreover, the present invention provides a method for creating a plant having resistance to pathogenic fungi, comprising incorporating a DNA sequence coding for a glucan elicitor receptor into a chromosome of a plant and expressing the gene in the plant. The present invention also provides a plant having resistance to pathogenic fungi, characterized in that a DNA sequence coding for a glucan elicitor receptor has been transferred into the plant and the gene is expressed in it.

The glucan elicitor receptor of the present invention is useful in the elucidation of resistance to fungi and the development of elicitor derivatives capable of inducing fungal resistance, and it can be used as an antigen for the production of antibodies against glucan elicitor receptors.

The DNA molecules of the present invention which contain nucleotide sequences coding for a glucan elicitor receptor and fragments thereof are useful as materials for establishing techniques for developing fungi-resistant plants. In other words, the DNA molecules of the present invention and fragments thereof may be introduced and expressed in various plants to enhance their fungal resistance.

Antibodies against the glucan elicitor receptor of the present invention, the DNA molecules of the present invention which contain nucleotide sequences coding for a glucan elicitor receptor, their mutants and anti-sense DNAs can be used in the studies of the elicitor-binding site of glucan elicitor receptor and signal transduction.

Further, the information on the amino acid sequence of glucan elicitor receptor and the nucleotide sequence coding therefor can be used in the studies of the elicitor-binding site of glucan elicitor receptor and the signal transduction in which glucan elicitor receptor is involved.

The plant of the present invention has high resistance to fungi.

BRIEF DESCRIPTION OF THE DRAWINGS

FIG. 2 shows the maps of plasmids pER23-1 and PER23-2.

FIG. 10 presents photographs showing the resistance of transformed tobacco plants to R. solani.

FIG. 14 shows the results of determination of the glucanase activity of a glutathione-S-transferase/kidney bean glucanase fusion protein.

DESCRIPTION OF THE PREFERRED EMBODIMENTS

Figure 1:
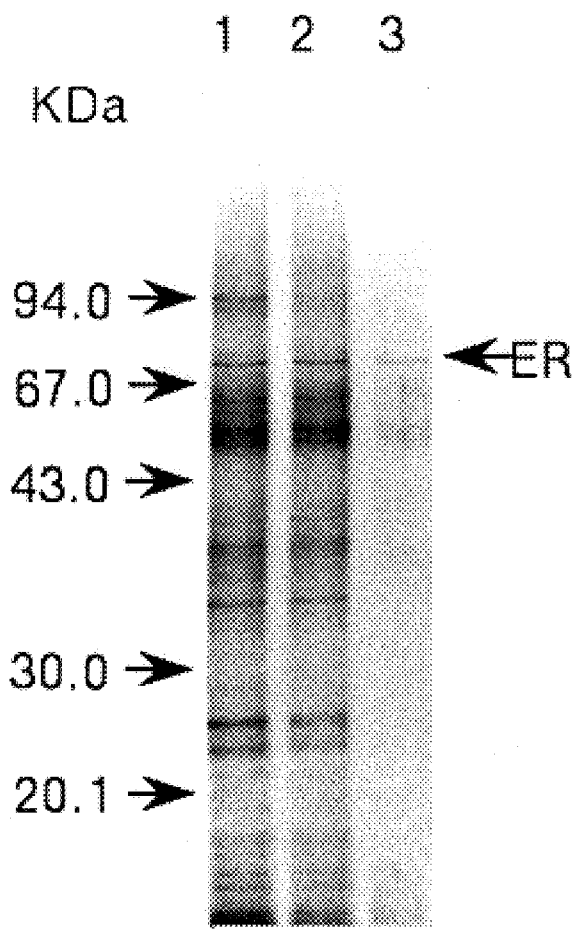
FIG. 1 shows SDS-polyacrylamide gel electrophoresis patterns of three purification steps.

Glucan elicitor receptor is a protein involved in the production of phytoalexins and which functions as a receptor for glucan elicitors derived from glucan, a cell wall component of fungi. Its function is to signal microsomes and nuclei to increase the phytoalexin content in cells; this function is effected through binding to a glucan elicitor generated by the cleavage of a part of mycelial walls of a pathogen by β-1,3-glucanase in plant cells when the pathogen, e.g. a microorganism of the genus Phytophthora has invaded into plant tissues.

The glucan elicitor receptor of the present invention has an amino acid sequence as substantially shown in SEQ ID NO:1. The "amino acid sequence as substantially shown in SEQ ID NO:1" includes amino acid sequences as shown in SEQ ID NO: 1 in which there may be the deletion, replacement or addition of an amino acid(s), provided that they maintain the function of a glucan elicitor receptor.

The glucan elicitor receptor of the present invention can be produced, for example, by a partially modified Cosio's method (E.J.B. (1992) 204: 1115). Briefly, the roots, leaves and stems of soybean, preferably variety green homer are homogenized and a membrane fraction is collected from the resulting slurry, purified by ion-exchange chromatography and further purified by affinity chromatography using an elicitor as a ligand. The elicitor used in the affinity chromatography is preferably derived from Phytophthora megasperma f. sp. glycinea race 1 (ATCC34566) because it shows incompatibility for green homer (i.e., resistance to the pathogen).

The amino acid sequence of the glucan elicitor receptor thus prepared can be determined as follows:

The purified glucan elicitor receptor is transferred on a PVDF membrane (Millipore Co.) by electroblotting and digested with lysylendopeptidase (AP-I). The fragmented peptides are recovered from the PVDF membrane and fractionated by reversed-phase HPLC ($\mu$-Bondasphere $5\mu$ C8). The peak fractions are analyzed with a gas-phase protein sequencer (Applied Biosystems Co.).

The glucan elicitor receptor of the present invention is useful in the elucidation of resistance mechanism of plants to fungi and the development of elicitor derivatives capable of inducing resistance to fungi, and it can be used as an antigen for the production of antibodies against glucan elicitor receptors.

The present invention encompasses DNA molecules containing nucleotide sequences coding for a glucan elicitor receptor, and fragments thereof. The DNA molecules of the present invention have preferably at least one stop codon (e.g., TAG) adjacent to the 3' end.

More specifically, the present invention encompasses DNA molecules containing nucleotide sequences coding for a glucan elicitor receptor having an amino acid sequence as substantially shown in SEQ ID NO: 1, and fragments thereof. The "DNA molecules containing nucleotide sequences coding for a glucan elicitor receptor" include all degenerate isomers. The term "degenerate isomers" means DNA molecules coding for the same polypeptide with different degenerate codons. If a DNA molecule having the nucleotide sequence of SEQ ID NO:2 is taken as an example, a DNA molecule in which a codon for any amino acid, e.g., AAC for Asn is changed to a degenerate codon AAT is called a degenerate isomer. Examples of such degenerate isomers include DNA molecules containing the nucleotide sequence shown in SEQ ID NO: 2.

In another aspect, the present invention provides DNA molecules containing nucleotide sequences coding for a glucan elicitor receptor, which are incorporated in plasmid pER23-1, and fragments thereof. E. coli DH5$_\alpha$ EKB633 transformed with plasmid pER23-1 was deposited with the National Institute of Bioscience and Human-Technology, the Agency of Industrial Science and Technology, on Jun. 15, 1994 under Accession Number FERM BP-4699 (1-3, Higashi 1-chome, Tsukuba-shi, Ibaraki-ken 305, JAPAN).

The DNA molecules of the present invention which contain nucleotide sequences coding for a glucan elicitor receptor and fragments thereof may optionally bind to an ATG codon for initiation methionine together with a translation frame in the upstream portion toward the 5' end and also bind to other DNA molecules having appropriate lengths as non-translation regions in the upstream portion toward the 5' end and the downstream portion toward the 3' end.

The DNA molecules of the present invention which contain nucleotide sequences coding for a glucan elicitor receptor and fragments thereof can be present typically in the form of parts of constituents of plasmid or phage DNA molecules or in the form of parts of constituents of plasmid, phage or genomic DNA molecules which are introduced into microorganisms (particularly, bacteria including E. coli and Agrobacterium), phage particles or plants.

In order to express stably the DNA sequences coding for a glucan elicitor receptor, or fragments thereof in plants, a promoter, a DNA molecule (ATG) encoding the initiation codon and a terminator may be added to the DNA sequences, or fragments thereof of the present invention in appropriate combinations. Examples of the promoter include the promoter of genes encoding ribulose-1,5-biphosphate carboxylase small subunit (Fluhr et al., Proc. Natl. Acad. Sci. USA (1986) 83: 2358), the promoter of a nopaline synthase gene (Langridge et al., Plant Cell Rep. (1985) 4:355), the promoter for the production of cauliflower mosaic virus 19S-RNA (Guilley et al., Cell (1982) 30:763), the promoter for the production of cauliflower mosaic virus 35S-RNA (Odell et al., Nature (1985) 313:810) and the like. Examples of the terminator include the terminator of a nopaline synthase gene (Depicker et al., J. Mol. Appl. Gen. (1982) 1:561) and the terminator of an octopine synthase gene (Gielen et al., EMBO J. (1984) 3:835).

The DNA molecule containing a nucleotide sequence coding for a glucan elicitor receptor can be obtained by a method comprising the steps of chemically synthesizing at least a part of the DNA molecule according to a conventional procedure of synthesis of nucleic acids and obtaining a desired DNA molecule from an appropriate cDNA library using the synthesized DNA molecule as a probe by a conventional method, for example, an immunological method or a hybridization method. Some plasmids, various kinds of restriction enzymes, T4 DNA ligase and other enzymes for use in the above method are commercially available. The DNA cloning, the construction of plasmids, the transfection of a host, the cultivation of the transfectant, the recovery of DNA molecules from the culture and other steps can be performed by the methods described in Molecular Cloning, J. Sambrook et al., CSH Laboratory (1989), Current Protocols in Molecular Biology, F. M. Ausubel et al., John Wiley & Sons (1987) and others.

More specifically, the DNA molecules of the present invention which contain nucleotide sequences coding for a glucan elicitor receptor can be obtained as follows:

Two kinds of partial amino acid sequences are selected from the amino acid sequences of a glucan elicitor receptor. Primers consisting of combinations of all bases which can encode the C terminus of the selected partial sequence and primers consisting of combinations of all bases which can encode the N terminus of the selected partial sequence are prepared. These synthesized primers are used as mixed primers to perform two PCR using DNA molecules of an appropriate soybean cDNA library as a template. Subsequently, two amplified fragments of given lengths whose amplification is expected (these fragments correspond to DNA molecules encoding the above two partial amino acid sequences) are picked up and the nucleotide sequences thereof are determined. On the basis of the determined nucleotide sequences, a primer having nucleotide sequences coding for the C terminus of an amino acid partial sequence positioned at the C terminal side of the glucan elicitor receptor and a primer having nucleotide sequences coding for the N terminus of an amino acid partial sequence positioned at the N terminal side of the glucan elicitor receptor are synthesized. These two synthesized primers are used to perform a PCR using the DNA molecules of the above soybean cDNA library as a template. The resulting amplified fragments are used as probes to hybridize the aforementioned soybean cDNA library, thereby yielding DNA molecules containing nucleotide sequences coding for the glucan elicitor receptor.

The obtained DNA molecules containing nucleotide sequences coding for the glucan elicitor receptor can be sequenced by any known methods, for example, the Maxam-Gilbert method (Methods Enzymol., 65:499, 1980), a dideoxynucleotide chain termination method using M13 phage (J. Messing, et al., Gene, 19:269, 1982) and the like.

Since the results of various studies on glucan elicitor suggest that a glucan elicitor receptor plays an important role in resistance to fungi in plants, it is expected that the DNA sequences coding for glucan elicitor receptor, or fragments thereof of the present invention can impart fungal resistance to plants if they are introduced and expressed in plant cells (particularly higher plant cells) which have no glucan elicitor receptor according to a conventional procedure. It has been proposed that fungi capable of infecting plants have generally suppressors, thereby acquiring an ability to suppress the fungal resistance of the plants. It is expected that new plants having resistance to fungi can be developed by introducing and expressing the DNA sequences coding for glucan elicitor receptor, or fragments thereof of the present invention such that the glucan elicitor receptor works or by modifying the DNA molecules or fragments thereof or by regulating their expression levels.

Moreover, if the DNA sequences coding for a glucan elicitor receptor, or fragments thereof of the present invention are introduced and expressed in plant cells, particularly in higher plant cells, together with fungal resistance enhancing genes or characters such as the gene of glucanase which imparts fungal resistance to plants, it is expected that higher fungal resistance can be imparted to plants than in the case where the gene of glucanase is introduced. Specific examples of a DNA molecule containing a nucleotide sequence coding for a glucanase include a DNA comprising a nucleotide sequence coding for a glucanase having an amino acid sequence as substantially shown in SEQ ID NO: 3 or 34. The "DNA comprising a nucleotide sequence coding for a glucanase" is intended to include all degenerate isomers. As a specific example of such degenerate isomers, a DNA comprising the nucleotide sequence as shown in SEQ ID NO: 4 or 33 may be mentioned.

Vectors used for introducing the DNA sequences coding for a glucan elicitor receptor, or fragments thereof may be constructed such that the glucan elicitor receptor can be stably expressed in plants. More specifically, a promoter, a DNA molecule encoding the initiation codon (ATG) and a terminator may be added to the DNA sequences coding for a glucan elicitor receptor, or fragments thereof in appropriate combinations. Examples of the promoter include the promoter of genes encoding ribulose-1,5-biphosphate carboxylase small subunit (Fluhr et al., Proc. Natl. Acad. Sci. USA (1986) 83:2358), the promoter of a nopaline synthase gene (Langridge et al., Plant Cell Rep. (1985) 4: 355), the promoter for the production of cauliflower mosaic virus 19S-RNA (Guilley et al., Cell (1982) 30:763), the promoter for the production of cauliflower mosaic virus 35S-RNA (Odell et al., Nature (1985) 313:810) and the like. Examples of the terminator include the terminator of a nopaline synthase gene (Depicker et al., J. Mol. Appl. Gen. (1982) 1:561) and the terminator of an octopine synthase gene (Gielen et al., EMBO J. (1984) 3:835).

The DNA molecules containing nucleotide sequences coding for a glucan elicitor receptor can be introduced into plant cells by any usual known methods, for example, the method described in "Plant genetic transformation and gene expression; a laboratory manual", J. Draper, et al. eds., Blackwell Scientific Publications, 1988. Examples of the methods include biological methods such as those using viruses or Agrobacteria and physicochemical methods such as electroporation, a polyethylene glycol method, microinjection, particle gun method, dextran method and the like.

When the plant to be transformed is a dicotyledonous plant, the method using Agrobacterium is generally preferable. When the plant to be transformed is a monocotyledonous plant or a dicotyledonous plant that is not susceptible to infection with Agrobacterium, a physical/chemical method such as electroporation is preferable. As a plant material into which a DNA of interest is to be transferred, an appropriate material may be selected from leaves, stems, roots, tubers, protoplasts, calluses, pollen, seed embryos, shoot primordia, etc. according to the method of transfer or the like.

When a DNA of interest is to be transferred into cultured plant cells, protoplasts are generally used as a material and the DNA is transferred thereinto by a physical/chemical method such as electroporation, the polyethylene glycol method or the like. On the other hand, when a DNA of interest is to be transferred into plant tissues, leaves, stems, roots, tubers, calluses, pollen, seed embryos, shoot primordia or the like are used as a material; preferably, leaves or stems are used. The DNA is transferred into such plant tissues by a biological method using a virus or Agrobacterium or a physical/chemical method such as the particle gun method, microinjection or the like; preferably, a biological method using Agrobacterium is used.

In order to regenerate a plant from those plant tissues or plant cells into which a DNA sequence coding for a glucan elicitor receptor has been transferred, these transformed plants or cells may be cultured in a medium such as hormone-free MS medium, if they are derived from tobacco. The resultant seedlings which are rooting may be transferred to soil to give grown-up plants.

As plants which can be imparted resistance or enhanced resistance to pathogenic fungi by transferring a DNA sequence coding for a glucan elicitor receptor, or a fragment thereof and expressing the gene by the methods described above, plants which are susceptible to infection with pathogenic fungi containing glucan in the cell walls may be mentioned. Specific examples of these plants include, but are not limited to, solanaceous plants and leguminous plants. More specifically, these plants include, but are not limited to, tobacco, soybean, potato, rice, chrysanthemum and carnation.

As pathogenic fungi, those containing glucan in the cell walls are embraced by the present invention. Specific examples of the pathogenic fungi include, but are not limited to, the genuses Phytophthora, Rhizoctonia, Pyricularia, Puccinia, Fusarium, Uromyces and Botrytis. More specifically, the pathogenic fungi include, but are not limited to, *Phytophthora nicotianae, Rhizoctonia solani, Pyricularia oryzae, Puccinia horiana, Fusarium oxysporum, Uromyces dianthi* and *Botrytis cinerea*.

According to the present invention, the DNA sequence coding for a glucan elicitor receptor, or fragments thereof transferred into a plant can be inherited to subsequent generations through seeds. Thus, the transferred DNA molecule is also present in those seeds which are formed from the pollen or ovaries of the plant of the invention, and the inherited character can be transmitted to the progeny. Accordingly, the plant of the invention into which a DNA sequence coding for a glucan elicitor receptor, or fragments thereof has been transferred can be propagated through seeds without losing its resistance to pathogenic fungi. The plant of the invention can also be propagated by a mass propagation method using plant tissue culture or by conventional techniques such as cutting, layering, grafting, division, etc. without losing its resistance to pathogenic fungi.

Whether a transformed plant has resistance to fungi or not can be examined by the following test methods.

Resistance to a Phytophthora fungus can be assayed by inoculating a fungal mycelium directly into plants and observing the expansion of lesions. Alternatively, the resistance may be assayed by inoculating zoospores from the fungus and observing the formation and expansion of lesions.

Resistance to a soil fungus can be assayed by mixing cultured fungal cells with soil, sowing seeds or setting plants on the soil, and observing a phenomenon of damping-off.

The present invention will now be explained in greater detail with reference to the following examples which are by no means intended to limit the scope of the present invention. In the following examples, a glucan elicitor receptor is abbreviated to "ER".

EXAMPLE 1

Purification of soybean root-derived glucan elicitor receptor
1) Measurement of glucan elicitor binding activity of ER A complex of an elicitor (average molecular weight: 10,000) and tyramine (TOKYO KASEI KOGYO CO., LTD.) was synthesized by the method of Jong-Joo Cheong (The Plant Cell (1991) 3: 127). The elicitor-tyramine complex was labelled with iodine using chloramine T.

A sample (protein amount <500 $\mu$g) was suspended in 500 $\mu$l of an assay buffer (50 mM Tris-HCl pH7.4, 0.1 M saccharose, 5 mM $MgCl_2$, 1 mM PMSF and 5 mM EDTA) and incubated at 0° C. for 2 hours. The iodine-labelled elicitor-tyramine complex in an amount of 7.0 nM (70 Ci/mmol, the number of moles is calculated on the assumption that the molecular weight of the elicitor is 10,000, and this applies to the following description) was added to the suspension and the mixture was incubated at 4° C. for 2 hours. The reaction solution was filtered through Whatman GF/B as treated with a 0.3% aqueous solution of polyethylene imine for at least 1 hour. The residue was washed 3 times with 5 ml of an ice-cold buffer (10 mM Tris-HCl pH 7.0, 1 M NaCl, 10 mM $MgCl_2$). The radio activity retained on the filter was counted with a gamma counter (count A). In order to eliminate the effect of non-specific binding, the same procedure as above was performed except that 17 $\mu$M of the elicitor was added to the same sample, the mixture was suspended in the assay buffer and the suspension was incubated at 0° C. for 2 hours. The obtained count was subtracted from the count A to give a count ($\Delta$ cpm) of elicitor-specific binding. The resulting count ($\Delta$ cpm) was divided by the total number of counts and then multiplied by the total amount of elicitor used in the experiment to calculate the amount of the elicitor-binding protein (in moles).

The purity of ER was checked by the above method.

2) Purification of soybean root-derived ER

Soybean (*Glycine max* cv. Green Homer) seeds (Takayama Seed Co.) were cultured on vermiculite for 1 week and then aquicultured for 15 days to harvest roots (about 40 kg, wet weight). The harvested roots were stored at −80° C. until they were used for the purification of ER. An ice-cold buffer (25 mM Tris-HCl pH 7.0, 30 mM $MgCl_2$, 2 mM dithiothreitol, 2.5 mM potassium metabisulfite and 1 mM PMSF) was added to the roots (2 kg, wet weight) in an amount of 1.25 L and the mixture was homogenized with a Waring Blender for 2 minutes.

The resulting slurry was filtered through a Miracloth (Calbiochem Co.) and the filtrate was centrifuged at 9,000 rpm at 4° C. for 15 minutes. The supernatant was ultracentrifuged at 37,000 rpm at 4° C. for 20 minutes. The precipitate was suspended in 160 ml of an ice-cold buffer (25 mM Tris-HCl pH 7.4, 0.1 M sucrose, 5 mM $MgCl_2$, 1 mM PMSF and 5 mM EDTA) to give a membrane fraction. An ampholytic detergent ZW3-12 (Boehringer Co.) was added to the membrane fraction to give a final concentration of 0.25% for solubilization of ER from the membrane fraction and the mixture was stirred at 8° C. for 30 minutes. The resulting mixture was ultracentrifuged at 37,000 rpm at 4° C. for 20 minutes to collect the supernatant containing the solubilized ER (soluble fraction). The soluble fraction (165 ml) was dialyzed against 2 l of a buffer (50 mM Tris-HCl pH 8.0, 0.2% ZW3-12, 4° C.) 4 times. Five milliliters of Protrap (TAKARA SHUZO CO., LTD.) was added to the sample and the mixture was stirred at 8° C. for 30 minutes to remove proteases from the sample and to stabilize ER. The resulting mixture was centrifuged at 2,800 rpm at 4° C. for 2 minutes to collect the supernatant. The obtained supernatant (160 ml) was concentrated to about 50 ml using an ultrafiltration membrane YM-10 (Amicon Co.) and the concentrate was dialyzed against an A buffer (50 mM Tris-HCl pH 8.0, 0.1 M sucrose, 5 mM $MgCl_2$, 1 mM PMSF, 5 mM EDTA and 0.2% ZW3-12, 4° C.).

The dialysate was applied to Q-Sepharose HP 26/10 (Pharmacia Co.) and ER was eluted in a linear gradient of 0–1 M NaCl (Q-Sepharose active fraction). The ER was eluted at a NaCl concentration of about 0.45 M. The Q-Sepharose active fraction was diluted 3 folds with A buffer and the diluted fraction was applied to Mono Q 10/10 (Pharmacia Co.). The ER was eluted in a linear gradient of 0–1 M NaCl (Mono Q active fraction, 8 ml). The ER was eluted at a NaCl concentration of about 0.25 M.

The ER was purified with an affinity gel using an elicitor as a ligand as follows:

Elicitor was prepared according to N. T. Keen with some modifications (Plant Physiol. (1983) 71: 460, Plant Physiol. (1983) 71: 466). Briefly, the mycelial wall of pathogenic *Phytophthora megasperma* f. sp. *glycinea* race 1 (ATCC34566) was treated with zymolyase 100T (KIRIN BREWERY CO., LTD.) to liberate an elicitor. After the treatment, Zymolyase 100T was eliminated by the adsorption on CM-cellulose packed in a column. The resulting passage-through fraction was purified with a gel permeation chromatography G-75 (Pharmacia Co.) to collect an elicitor fraction whose average molecular weight was 10,000 Da. The glyceollin-inducing elicitor activity of the collected fraction was determined by the method of M. Yoshikawa (Nature (1978) 257:546). The addition of 8 $\mu$g of the elicitor to soybean cotyledons resulted in the induction of about 550 $\mu$g of glyceollin after 24 hours incubation.

In order to eliminate non-specific adsorption on the gel carrier, Mono Q active fraction was collected and stirred with about 33 mg of maltose-coupled glass gel (bed volume: about 100 $\mu$l) at 8° C. for 1 hour. The gel was precipitated by centrifugation (1,000 rpm, 4° C., 2 minutes) to collect the supernatant (maltose-coupled glass gel passage-through fraction). The maltose-coupled glass gel was prepared by the method of A. M. Jeffrey et al. (Biochem. Biophys. Res. Commun. (1975) 62: 608). Briefly, 120 mg of maltose and 6 g of Glass Aminopropyl (Sigma Co.) were suspended in 36 ml of $H_2O$ and the suspension was stirred at room temperature overnight. To the resulting suspension was added 36 ml of ethanol. Immediately thereafter a solution of sodium borohydride (864 mg) in ethanol (72 ml) was added to the mixture. The resulting mixture was sonicated for 2 minutes and stirred at room temperature for 5 hours. Water (288 ml) was added to the reaction mixture and the resulting mixture was cooled with ice and adjusted to pH 5.6 with acetic acid. The gel was washed with about 1.8 L of $H_2O$ to remove the free maltose. Maltose contained in the washing solution was determined quantitatively by the method of J. H. Roe (J. Biol. Chem. (1955) 212:335) using an anthrone reagent. An amount of the gel-coupled maltose was estimated from the amount of the maltose contained in the washing solution. As a result, it was found that 60 mg of maltose was coupled to 6 g of Glass Aminopropyl.

About 17 mg of the elicitor-coupled glass gel (bed volume: about 50 $\mu$l) was added to 8 ml of the maltose-coupled glass gel passage-through fraction and the mixture was stirred gently at 8° C. overnight. The gel was collected by centrifugation (1,000 rpm, 4° C., 2 minutes) and washed with 2 bed volumes of A buffer 2 times. The gel was washed additionally with 4 bed volumes of 0.1% SDS 3 times to collect gel-coupled ER (elicitor-coupled glass gel eluted fraction). The elicitor-coupled glass gel was prepared by the method of A. M. Jeffrey et al. (Biochem. Biophys. Res. Commun. (1975) 62: 608). Briefly, elicitor (37 mg) and Glass Aminopropyl (490 mg) were suspended in 6 ml of $H_2O$ and stirred at room temperature overnight. Ethanol (6 ml) was added to the suspension and a solution of sodium borohydride (144 mg) in ethanol (12 ml) was added immediately thereafter. The mixture was sonicated for 2 minutes and stirred at room temperature for 5 hours. To the resulting mixture was added 48 ml of $H_2O$. The mixture was cooled with ice and adjusted to pH 5.6 with acetic acid. The free elicitor was determined quantitatively with an anthrone reagent. The amount of the gel-coupled elicitor was estimated from the amount of the free elicitor contained in the washing solution. As a result, it was found that 34 mg of the elicitor was coupled to 490 mg of Glass Aminopropyl.

The protein and ER amounts in the above steps for purification are summarized in Table 1.

TABLE 1

Protein and ER Amounts in the Steps for Purification
(Soybean roots weighing 40 kg on a wet basis were used as a starting material)

|  | Protein (mg) | ER (pmol) |
| --- | --- | --- |
| Membrane Fraction | 17900 | 30 |
| Soluble Fraction | 2000 | 214 |
| Q-Sepharose Active Fraction | 190 | 205 |
| Mono Q Active Fraction | 49 | 233 |
| Maltose-Coupled Glass Gel Passage-through Fraction | 45 | 220 |
| Elicitor-Coupled Glass Gel Eluted Fraction | 0.004* | 45 |

*Estimated from the band intensity obtained by silver stain after SDS-PAGE.

The Mono Q active fraction, passage-through fraction from maltose-coupled glass gel and eluted fraction from elicitor-coupled glass gel (10 µl each) were electrophoresed on an electrophoretic gradient gel, SDS-PAGE plate 10/20 (Daiich Kagaku Yakuhin Co.) and stained with silver (Daiich Kagaku Yakuhin Co.) The electrophoresis patterns are shown in FIG. 1. In FIG. 1, lane 1 is the Mono Q active fraction, lane 2; the passage-through fraction from the maltose-coupled glass gel and lane 3; the eluted fraction from the elicitor-coupled glass gel. FIG. 1 shows that the ER bands were detected at a molecular weight of about 70,000 Da.

The protein of about 70,000 in molecular weight was labelled with iodine-125 by using an $^{125}$I-labelled complex of a photoaffinity reagent SASD (Pierce Co.) and the elicitor. The SDS-PAGE band of the membrane fraction was transferred on a PVDF membrane by western blotting and incubated with the same $^{125}$I-labelled elicitor as used in measuring the elicitor-binding activity of ER on the PVDF membrane so that the protein of about 70,000 Da in molecular weight was labeled with iodine-125. These facts reveal that the protein of about 70,000 Da in molecular weight had an elicitor-binding activity.

About 4 µg of ER was purified from about 40 kg by wet weight of the soybean root by the above method.

3) Analysis of ER-fragmented peptides

The ER was fragmented by protease digestion to peptides. The amino acid sequences of the fragmented peptides were determined by the method of Iwamatsu (Akihiro Iwamatsu, Seikagaku (1991) 63: 139, A. Iwamatsu, Electrophoresis (1992) 13: 142). A solution of the ER purified by the above method was concentrated to about 100 µl with Centricon-30 (Amicon Co.) and subjected to a 10–20% polyacrylamide SDS electrophoresis. The resulting protein bands were transferred on a PVDF membrane (Millipore Co.) with an electroblotting apparatus (Sartrius Co.). The bands transferred on the PVDF membrane were stained with 0.1% Ponceau S (Sigma Co.)/1% acetic acid. The main band of 70,000 Da in molecular weight was sectioned and decolored with 0.5 mM NaOH. This band was reductively S-carboxymethlated. Lysylendopeptidase (AP-1) was added to the resulting band at an enzyme:substrate (mol:mol) ratio of 1:100 and the mixture was reacted at 30° C. for 16 hours. The resulting fragmented peptides were applied to a µ-Bondasphere 5µ C8-300 Å (2.1×150 mm, Waters) column equilibrated with 98% solvent A and 2% solvent B and eluted in a 2–50% linear gradient of solvent B for 30 minutes at a flow rate of 0.25 ml/minute (solvent A: 0.05% TFA solution, solvent B: 0.02% TFA in 2-propanol:acetonitrile=7:3 (v/v)). Eluted peptides were detected by absorbance at 214 nm and each peak fraction was collected manually. The obtained peak fractions were analyzed with a gas-phase protein sequencer (Model 470A of Applied Biosystems). As a result of analysis of all the peak fractions obtained, the following amino acid sequences of the fragmented peptides were clearly determined.

1: Val Asn Ile Gln Thr Asn Thr Ser Asn Ile Ser Pro Gln (N-terminus) (SEQ ID NO:5)
5: Lys Ser Ile Asp Gly Asp Leu Val Gly Val Val Gly Asp Ser (SEQ ID NO:6)
6: Lys Tyr Lys Pro Gln Ala Tyr Ser Ile Val Gln Asp Phe Leu Asn Leu Asp (SEQ ID NO:7)
7: Lys Thr Asp Pro Leu Phe Val Thr Trp His Ser Ile Lys (mix sequence) (SEQ ID NO:8)

EXAMPLE 2

Cloning of soybean ER gene

1) Preparation of soybean mRNA

Soybean (*Glycine max* cv. Green Homer) seeds (Takayama Seed Co.) were cultured on vermiculite for 1 week and aquicultured for 15 days to harvest roots (about 40 kg, wet weight). A portion of the harvested roots was stored at −80° C. until it was used. Total RNA was obtained by the method of Ishida (Cell Technology Laboratory Manipulation Manual, Kodansha Scientific). Briefly, the stored roots (28.5 g, wet weight) were ground on a mortar while adding liquid nitrogen. To the obtained powder, 35.6 ml of a GTC solution held at 65° C. was added and the mixture was homogenized with a Waring Blender. The resulting suspension was centrifuged at 6,000 rpm at room temperature for 15 minutes to collect 40 ml of the supernatant. The supernatant was layered gently on a cushion solution of cesium in a centrifuge tube and centrifuged at 35,000 rpm at 25° C. for 20 hours. The resulting precipitate was dissolved in 9 ml of TE/0.2% SDS. After phenol/chloroform extraction was conducted 2 times, total RNA (4.37 mg) was recovered by ethanol precipitation.

The obtained total RNA (2.2 mg) was used for purification with oligotex dT30 (Japan Roche Co.) according to the manual and then 68 µg of purified poly(A)+RNA was obtained.

2) Preparation of soybean cDNA library cDNA molecules were synthesized from 5 µg of the poly(A)+RNA with a cDNA synthesis kit (Pharmacia Co.) according to the manual. The synthesized cDNA fragments were ligated to lambda phage vector λ gt10 (Stratagene Co.) with T4 ligase (TAKARA SHUZO CO., LTD.). Gigapack (Stratagene Co.) was used to package a DNA mixture into the phage particles to prepare a soybean cDNA library of about 1.5×10⁶ pfu. The library was amplified to 160 ml of a soybean cDNA library of 1.6×10¹¹ pfu/ml.

Total DNA in the cDNA library was prepared as follows:
Chloroform/isoamylalcohol (24:1) was added to 500 µl of a phage solution (1.6×10¹¹ pfu/ml) in an equal amount. The mixture was shaken for 30 seconds and centrifuged to collect the aqueous layer. The aqueous layer was extracted again with chloroform/isoamylalcohol (24:1). To the resulting aqueous layer were added 5 µl of a 3 M sodium acetate solution (pH 5.4) and 125 µl of ethanol and the mixture was centrifuged to collect the precipitate. The precipitate was washed with a 70% ethanol solution and dissolved in a 10 mM Tris-HCl solution (pH 8) containing 1 µg/ml RNase A (Sigma Co.). This solution was used as a PCR template.

3) Amplification and Cloning of Soybean ER cDNA Fragments by PCR

The following four oligodeoxynucleotides (mixed primers U5, U7, U10 and U12) were synthesized with an automatic nucleic acid synthesizer (Model 394 of Applied Biosystems Co.) on the basis of the amino acid sequences of the fragmented peptides obtained in Example 1 (#5 and #6):

Primer U5 5'-AARAGYATHGAYGGNGA-3' (SEQ ID NO:9)
Primer U7 5'-WRTCNCCNACNAC-3' (SEQ ID NO:10)
Primer U10 5'-GTNAAYAARATNCARAC-3' (SEQ ID NO:11)
Primer U12 5'-ARRTTNAGRAARTCYTC-3' (SEQ ID NO:12)
(R:A/G, Y:C/T, W:A/T, H:A/C/T, N:A/G/T/C)

The total DNA in 0.5 µg of the cDNA library was dissolved in 79 µl of distilled water. Either a combination of primers U5 and U7 or a combination of primers U10 and U12 (100 pmol each) and 0.5 µl of Taq DNA polymerase (TAKARA SHUZO CO., LTD.) were added to 8 µl of 2.5 mM dNTP in 10 µl of a 10×PCR buffer (attached to Taq DNA polymerase of TAKARA SHUZO CO., LTD.) to give a final amount of 100 µl. PCR reaction was performed with a Gene Amp PCR System 9600 (Perkin-Elmer Co.) by 50 cycles of 1) denaturation at 94° C.×30 seconds, 2) renaturation at 47° C.×30 seconds and 3) elongation at 72° C.×1 minute. After the reaction, 15 μl of the reaction solution was electrophoresed on a 15% polyacrylamide gel. The gel was stained with a 0.5 μg/ml ethidium bromide solution for 10 minutes. The bands showing specifically amplified fragments of 40 bp and 47 bp whose amplification was expected were sectioned while observing under UV light. The gel sections were ground with a plastic bar and eluted with an elution buffer (0.5 M ammonium acetate, 10 mM magnesium acetate, 1 mm EDTA and 0.1% SDS) overnight to collect a DNA-containing solution.

The collected DNA fragments were cloned into plasmid pT7Blue(R) with a pT7Blue T-Vector Kit (Novagene Co.). The obtained plasmids p#5-1, 2, and p#6-1, 2, 3, 4, 5, 6, 7, 8 and 9 were sequenced with a fluorescence automatic DNA sequencer (Model 373A of Applied Biosystems Co.). The results showed that the resulting amplified DNA fragments other than the primers also encoded the amino acid sequences of fragmented peptides #5 and #6.

The following two oligodeoxynucleotides (mixed primers U18 and U19) were synthesized with an automatic nucleic acid synthesizer on the basis of the results of the DNA sequencing.
Primer U18 5'-AAGTAYAAGCCRCAAGCCTATTCA-3' (SEQ ID NO:13)
Primer U19 5'-ATCGCCRACAACMCCAA-3' (SEQ ID NO:14)
(Y and R are as defined above, M:A/C)

The total DNA in 0.5 μg of the cDNA library was dissolved in 79 μl of distilled water. A combination of primers U18 and U19 (100 pmol each) and 0.5 μl of Taq DNA polymerase were added to 8 μl 2.5 mM dNTP in 10 μl of a 10×PCR buffer to give a final amount of 100 μl. PCR reaction was performed by 40 cycles of 1) denaturation at 94° C.×30 seconds, 2) renaturation at 52° C.×30 seconds and 3) elongation at 72° C.×1 minute. Fifteen microliters of the reaction solution was electrophoresed on a 1% agarose gel.

The gel was stained with a 0.5 μg/ml ethidium bromide solution for 15 minutes. The band showing a specifically amplified fragment of about 540 bp was sectioned while observing under UV light. The gel section was treated with Gene Clean II (Bio101 Co.) to collect a DNA-containing solution.

The collected DNA fragment was cloned into plasmid pT7Blue(R) with a pT7Blue T-Vector Kit. The obtained plasmid p#5-#6 was sequenced with a fluorescence sequencer. The results showed that the amplified DNA fragment consisted of 539 bp and encoded not only the amino acid sequences of fragmented peptides #5 and #6 at the both sides, but also peptide #7 in the amplified portion.

4) Screening and Cloning of Library by Hybridization

Plasmid #5-#6 into which the ER cDNA fragment was cloned was digested with restriction enzymes BamHI and PstI. A DNA fragment of about 540 bp was recovered and used as a probe. The recovered DNA fragment was labelled with [α-$^{32}$P] dCTP using a Megaprime DNA labelling system (Amersham Co.) according to the manual and the reaction solution was used in a hybridization experiment.

A phage of the cDNA library was infected with E. coli C600 hfl (Invitrogen Co.) and inoculated in a 10 mg/ml MgCl$_2$-containing L medium on plates of about 15 cm in diameter to form a total of about 1×10$^6$ of plaques. The plaques were blotted on a nylon membrane (Hybond-N; Amersham Co.). The membrane was reacted with the $^{32}$P-dCTP labeled ER cDNA fragment and positive phages detected by autoradiography were screened again in the same way to give about 30 phage clones having different signal intensities. Clone λ ER23 having the longest inserted DNA fragment was selected.

The λ phage DNA molecule was purified with a LambdaSorb (Promega Co.) from a solution of the positive clone λ ER23 isolated in the hybridization experiment. Ten microliters of a 10×EcoRI cleavage buffer (restriction enzyme EcoRI 10 U) was added to 5 μg of the DNA solution to give a total amount of 100 μl and the mixture was reacted at 37° C. overnight. The reaction solution was electrophoresed on a 1% agarose gel. A band of about 2.3 kb was sectioned and treated with a Gene Clean II (Bio101 Co.) to collect a DNA-containing solution. Vector pBluescriptII KS- (0.02 μg) (Stratagene Co.) was cleaved with restriction enzyme EcoRI.

After the two DNA solutions were mixed, 2 μl of a 10×ligase buffer and 0.2 μl of T4 DNA ligase (TAKARA SHUZO CO., LTD) were added to give a total amount of 20 μl. The mixture was reacted at 16° C. for 4 hours and the reaction mixture solution was used to transform E. coli DH5$_\alpha$ (Gibco BRL Co.). A 2% agar plate medium was prepared with 25 ml of an L medium containing 50 μg/ml ampicillin, 40 μg/ml IPTG and 40 μg/ml X-gal. The transformed E. coli was inoculated on the agar plate medium and grown at 37° C. overnight. White colonies were selected from the formed colonies and cultured in 3 ml of an L medium containing 50 μg/ml ampicillin at 37° C. for 8 hours. Plasmids were recovered from these bacterial cells by an alkaline method and determined whether they were clones into which a desired fragment was cloned with the restriction enzyme, thereby giving plasmids pER23-1 and pER23-2 (5225 bp) which had opposite orientations to the vector. The maps of plasmids pER23-1 and pER23-2 are shown in FIG. 2.

5) Determination of the Nucleotide Sequence of the ER-encoding Clone

The DNA nucleotide sequences of plasmids pER23-1 and pER23-2 were determined in both orientations with a fluorescence sequencer by 1) using plasmids pER23-1 and pER23-2 digested by appropriate restriction enzymes, 2) using appropriate primers synthesized on the basis of the information about already determined nucleotide sequences, or 3) cleaving pER23-1 with restriction enzymes KpnI and XhoI and pER23-2 with restriction enzymes KpnI and ClaI and then using a kilosequence deletion kit (TAKARA SHUZO CO., LTD) to prepare plasmids having a deletion at intervals of about 200–300 bp. The DNA nucleotide sequence is shown in SEQ ID NO: 2 of the SEQUENCE LISTING. The results showed that the DNA fragment contained a 667 amino acid-encoding open reading frame of 2001 bp beginning at a nucleotide sequence corresponding to the N-terminal sequence (fragmented peptide #1) sequenced with the amino acid sequencer. The amino acid sequence is shown in SEQ ID NO: 1 of the SEQUENCE LISTING. The amino acid sequence deduced from the resulting DNA nucleotide sequence was consistent with the previously determined amino acid sequence of the soybean ER.

In addition, highly homologous amino acid sequences were searched for with a nucleic acid and amino acid sequence analysis software package (Macvector: Kodak Co.) using a nucleic acid and amino acid sequence data base (Entrez: NCBI). However, no amino acid sequences were found to be highly homologous to the heretofore known sequences. Hence, it is clear that the prepared ER is a novel protein.

EXAMPLE 3
Expression of the Soybean ER in Tobacco Plants
1) Construction of Plant Expression Plasmid pKV1-ER23

Figure 3:
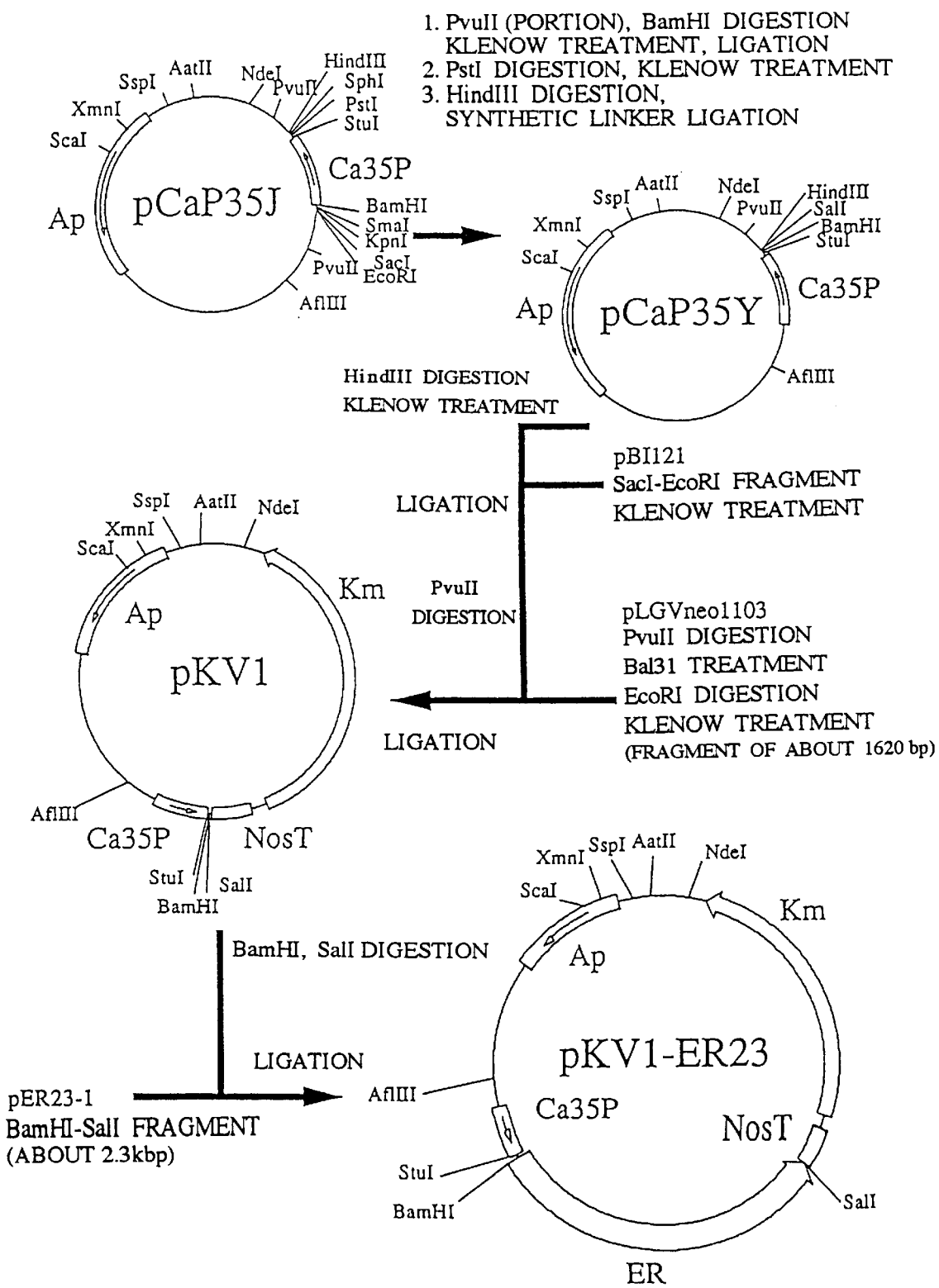
FIG. 3 shows the procedure for constructing plasmid pKV1-ER23.

As shown in FIG. 3, a plant expression vector pKV1 to be used in this example was prepared from cauliflower mosaic virus 35S promoter-containing plasmid pCaP35J (J. Yamaya et al. (1988) Mol. Gen. Genet. 211:520) as follows:

Plasmid pCaP35J was digested completely with restriction enzyme BamHI to delete a multi-cloning site present upstream of the 35S promoter. Following partial digestion with PvuII, a treatment was conducted with Klenow fragments (TAKARA SHUZO CO., LTD) to make blunt ends. The resulting plasmid DNA was circularized by ligation and introduced into $E.$ $coli$ $DH5_\alpha$. A desired plasmid was selected from the resulting clones. The selected plasmid was digested with restriction enzyme PstI to insert a multi-cloning site present downstream of the 35S promoter. A treatment was conducted with Klenow fragments to make blunt ends. The resulting plasmid DNA was digested with HindIII. The following synthetic linker DNAs were synthesized with an automatic nucleic acid synthesizer, annealed and ligated to the HindIII-digested plasmid. The resulting plasmid DNA was introduced into $E.$ $coli$ $DH5_\alpha$. Desired plasmid pCaP35Y (2837 bp) was selected from the obtained clones.

5'-GGAATTCGAGCTCGGTACCCGGGGGATCCTCTAG AGTCGACCTGCAGGCATGCA-3' (SEQ ID NO: 15)
5'-CCTTAAGCTCGAGCCATGGGCCCCCTAGGAGATC TCAGCTGGACGTCCGTACGTTCGA-3' (SEQ ID NO:16)

In order to introduce a terminator of nopaline synthase into the pCaP35Y, plasmid pBI121 (Clontech Co.) was digested with SacI and EcoRI and the SacI-EcoRI fragment was treated with Klenow fragments to make blunt ends; then, the resulting fragment of pBI121 was ligated to plasmid pCaP35Y in which blunt ends were made at a HindIII site downstream of the 35S promoter. The resulting plasmid DNA was introduced into $E.$ $coli$ $DH5_\alpha$. A desired plasmid was selected from the obtained clones. In order to introduce a kanamycin-resistance cassette into the selected plasmid, the latter was digested with PvuII and ligated to a fragment (about 1620 bp) of pLGVneo1103 (R. Hain et al. (1985) Mol. Gen. Genet. 199: 161) that was obtained by the steps of cleavage at a PvuII site present downstream of the octopine synthase terminator, treatment with Ba131 (TAKARA SHUZO CO., LTD) to make a deletion, cleavage at a EcoRI site upstream of a nopaline synthase promoter, and the creation of a blunt end at both ends. The resulting plasmid DNA was introduced into $E.$ $coli$ $DH5_\alpha$. Desired plasmid, or plant expression vector pKV1 (4828 bp), was selected from the obtained clones.

The prepared pKV1 was digested at unique sites by restriction enzymes BamHI and SalI and ligated to the ER gene-containing fragment (i.e., the BamHI-SalI fragment of pEB23-1, about 2.3 kbp). The resulting plasmid DNA was introduced into $E.$ $coli$ $DH5_\alpha$. Desired ER-expression plasmid pKV1-ER23 (about 7.1 kbp) was selected from the obtained clones.

2) Transient Expression of ER in Cultured Tobacco Cells

The ER gene was introduced into cultured tobacco cells by electroporation for transient ER expression by a partial modification of Watanabe's method (Y. Watanabe (1987) FEBS 219: 65). The DNA molecules of the plasmid pKV1-ER23 were purified by an alkaline method. Cultured tobacco cells were obtained by the method of Hirai et al. (Plant Cell Cultivation Manual, Gakkai Shuppan Center, 1982) for use in the transient expression of ER. Tobacco seeds (variety Bright Yellow, provided by Professor Hirofumi Uchimiya of University of Tokyo) were sterilized with a 1% sodium hypochlorite solution and then germinated. The tobacco juvenile tissues just after the germination were transplanted in a tobacco cultivation agar medium (Murashige-Skoog medium (Flow Laboratories Co.) supplemented with 2 ppm 2,4-dichlorophenoxyacetic acid, 3% sucrose and 8% agar) to induce calluses after 3 weeks. About 1 g of callus masses were suspended in 50 ml of a tobacco cultivation medium (Murashige-Skoog medium (Flow Laboratories Co.) supplemented with 2 ppm 2,4-dichlorophenoxyacetic acid and 3% sucrose) to prepare cultured cells. These tobacco cells were cultured until they entered a logarithmic growth phase. The cultured cells were collected by centrifugation (600 rpm, 3 minutes) and suspended in a solution consisting of 1% cellulase Onozuka (Yakult Co.), 1% Dricelase (Kyowa Hakko Co., Ltd.), 0.1% Pectriase (Seishin Seiyaku Co.) and 0.4 M D-mannitol (Wako Pure Chemicals Co., Ltd.) and which was adjusted to pH 5.7 with HCl. Reaction was performed at 30° C. for 90 minutes to prepare protoplasts. The reaction solution was washed with 0.4 M D-mannitol at 4° C. by 3 cycles of centrifugation to remove the enzyme solution. The operation of electroporation consisted of suspending $1\times10^6$ cells in 0.8 ml of an electroporation solution (70 mM KCl, 5 mM MES and 0.3 M mannitol), mixing the suspension with 10 µg of the DNA molecules of pKV1-ER23 and treating the mixture with a genepluser (Biorad Co.) at 125 µF and 300 V in an electroporation cuvette (Biorad Co., electrode spacing: 0.4 cm). After the treatment, the solution was collected with a pasteur pipet and left to stand on ice for 30 minutes. Reaction was performed at 30° C. for 5 minutes and the reaction solution was resuspended in a protoplast medium (Murashige-Skoog medium (Flow Laboratories Co.) supplemented with 0.2 ppm 2,4-dichlorophenoxyacetic acid, 1% sucrose and 0.4 M mannitol and adjusted to pH 5.7). The cells were left to stand in the dark at 25° C. overnight and collected by centrifugation (8,000 rpm, 3 minutes). Sixty microliters of a suspension buffer (25 mM Tris-HCl pH7.0, 30 mM $MgCl_2$, 2 mM dithiothreitol, 2.5 mM potassium metabisulfite and 1 mM PMSF) were added to the cells and the mixture was stirred on a vortex for 3 minutes. The resulting sample was stored at −80° C. until an elicitor-binding experiment was conducted.

For control, the above procedure was repeated except that the DNA molecule of pKV1 instead of pKV1-ER23 was introduced into tobacco cells.

3) Stable Expression of ER in Tobacco Suspension Cultured Cells

Transformed cultured tobacco cells capable of constant ER gene retention were selected as follows from the cultured tobacco cells capable of transient ER expression:

The protoplasts obtained in the preparation of the cultured tobacco cells capable of transient ER expression were suspended in a 1% agarose-containing protoplast medium (Murashige-Skoog medium (Flow Laboratories Co.) supplemented with 0.2 ppm 2,4-dichlorophenoxyacetic acid, 1% sucrose and 0.4 M mannitol and adjusted to pH 5.7). The suspension was dropped on a plate with a dropping pipet before the agarose was solidified, whereby the protoplasts were fixed in the bead-like solid medium. After the agarose was solidified, an agarose-free protoplast medium was added to the plate, thereby immersing the protoplast-fixing agarose medium in the liquid medium. After the protoplasts were cultured in the dark for 1 week, kanamycin was added to a final concentration of 100 µg/ml and the cultivation was continued. Transformants selected from the grown colonies were transferred in a kanamycin-containing liquid medium and cultured.

Two clones (I 1 and I 6) of cultured tobacco cells stably transformed by pKV1-ER23 and two clones (C 2-1 and C 2-4) of cultured tobacco cells stably transformed by pKV1 were obtained.

4) Elicitor-binding Activity Experiment

The elicitor-binding activity was measured as follows:

A complex of an elicitor and tyramine (TOKYO KASEI KOGYO CO., LTD.) was synthesized by the method of Jong-Joo Cheong (The Plant Cell (1991) 3: 127). The elicitor-tyramine complex was labelled with iodine-125 using chloramine T. The resulting sample (protein amount <500 µg) was suspended in 500 µl of an assay buffer (50 mM Tris-HCl pH7.4, 0.1 M saccharose, 5 mM $MgCl_2$, 1 mM PMSF and 5 mM EDTA) and incubated at 0° C. for 2 hours. The iodine-labelled elicitor-tyramine complex in an amount of 100 nM (70 Ci/mmol) was added to the suspension and the mixture was incubated at 4° C. for 2 hours. The reaction solution was filtered through Whatman GF/B (as treated with a 0.3% aqueous solution of polyethylenimine for at least 1 hour) and washed 3 times with 5 ml of an ice-cold buffer (10 mM Tris-HCl pH 7.0, 1 M NaCl, 10 mM $MgCl_2$). The radio activity retained on the filter membrane was counted with a gamma counter (count A). In order to eliminate the effect of non-specific binding, the same procedure as above was performed except that 17 µM of the elicitor was added to the same sample, the mixture was suspended in the assay buffer and the suspension was incubated at 0° C. for 2 hours. The obtained count was subtracted from the count A to give a count (Δ cpm) of elicitor-specific binding. The resulting count (Δcpm) was divided by the total number of counts and then multiplied by the total amount of elicitor used in the experiment to calculate the amount of the elicitor-binding protein (in moles).

As a result, a specific binding to the elicitor was observed in the tobacco cells transformed with the DNA molecule of pKV1-ER23, whereas no specific binding to the elicitor was observed in the control tobacco cells in which the DNA molecule of pKV1 was introduced (Table 2). This fact reveals that the gene obtained above encodes a protein having the elicitor-binding activity.

TABLE 2

Elicitor-binding Activity of Cultured Tobacco Cells

| Fraction | Transforming DNA | Binding Activity (fmol/mg) |
|---|---|---|
| Transient Expression | pKV1 | <0 |
|  | pKV1-ER23 | 90.5 |
| Stable Expression |  |  |
| C2-1 | pKV1 | <0 |
| C2-4 | pKV1 | <0 |
| I 1 | PKV1-ER23 | 150 |
| I 6 | pKV1-ER23 | 196 |

5) Transient Increase in Intracellular $Ca^{2+}$ Concentration in Transformed Tobacco Cultured Cells by Addition of Glucan Elicitor Plants recognize the elicitor by a specific receptor thereto and then promote the accumulation of phytoalexin or induce hypersensitive reaction to prevent fungus invasion. It has been reported for some plants that the inflow of calcium ion into cells in the early phase of such resistance reactions is important (U. Conrath et al. (1991) FEBS LETTERS 279: 141, M. N. Zook et al. (1987 ) Plant Physiol. 84: 520, F. Kurosaki et al. (1987 ) Phytochemistry 26: 1919; C. L. Preisig and R. A. Moreau (1994) Phytochemistry 36: 857). A report has also been made suggesting that the inflow of calcium ion into cells triggers the promotion of the phytoalexin accumulation in soybean which the present inventors used to obtain ER (M. R. Stab and J. Ebel (1967) Archi. Biochem. Biophys. 257: 416). Hence, if a transformed cultured tobacco cell is prepared by introducing the ER gene into an ER-free tobacco cultured cell to express the ER and if the intracellular calcium ion concentration is changed by the addition of a glucan elicitor, the change is anticipated to trigger a resistance reaction by the glucan elicitor in plants other than soybean (e.g., tobacco), thereby allowing them to show resistance to a wide variety of fungi which use glucan as a mycelial wall component.

The change in intracellular $Ca^{2+}$ concentration of transformed cultured tobacco cells by the addition of the elicitor was examined.

In this experiment, the transformed cultured tobacco cells (I 6) obtained by the kanamycin selection and the plasmid-containing cultured tobacco cells (C 2-4) were used.

The intracellular $Ca^{2+}$ concentrations of the cultured cells were measured as follows with an acetoxymethyl derivative (Fura-2 AM) of a fluorescence chelator (Fura-2) for $Ca^{2+}$ measurement:

Cells were harvested from about 2 ml of the transformed tobacco cell culture (corresponding to a cell volume of about 250 µl after standing for 10 minutes) by centrifugation (600 rpm, 30 seconds) and the supernatant was removed. To the cells was added 2 ml of a tobacco cultivation medium and the mixture was stirred gently and centrifuged (600 rpm, 30 seconds) to remove the supernatant. The same operations were repeated to wash the cultured cells. The washed cultured cells was suspended homogeneously in 2 ml of the medium. To 1 ml of the suspension of the cultured cells in the medium, 1 ml of the medium and 4 µl of 1 mM Fura-2 AM (final concentration: 2 µM, Dojin Chemical Co.) were added and the mixture was incubated in the dark for 30 minutes with occasionally stirring. Subsequently, the cells were washed 2 times with 2 ml of the medium by centrifugation (600 rpm, 30 seconds) to eliminate the free Fura-2 AM which was not incorporated into the cells. The washed cultured cells were suspended in 2 ml of the medium homogeneously and the suspension (2 ml) was transferred into a fluorescence-measurement cell. The incorporated Fura-2 AM should be changed to Fura-2 by hydrolysis with intracellular esterase. The fluorescence produced by the binding of Fura-2 to intracellular $Ca^{2+}$ was measured at a fluorescence wavelength of 505 nm under exciting light of 335 nm with the cultured cells being stirred to ensure against precipitation of the cultured cells. The change in intracellular $Ca^{2+}$ concentration was examined by measuring the fluorescence intensity at specified intervals of time after the addition of 50 µl of glucan elicitor (1 mg/ml) or deionized water to the cultured cells. For control, the change in intracellular $Ca^{2+}$ concentration was examined on the plasmid-containing cultured tobacco cells by the same method as above. For another control, the change in intracellular $Ca^{2+}$ concentration was examined on cultured soybean cells by the same method as above, except that the cultured cells were washed with a medium for soybean cells having the following formulation. $NaH_2PO_4.H_2O$ 75 mg/ml, $KH_2PO_4$ 170 mg/ml, $KNO_3$ 2,200 mg/ml, $NH_4NO_3$ 600 mg/ml, $(NH_4)_2SO_4$ 67 mg/ml, $MgSO_4.7H_2O$ 310 mg/ml, $CaCl_2.2H_2O$ 295 mg/ml, $FeSO_4.7H_2O$ 28 mg/ml, $EDTA.Na_2$ 37.3 mg/ml, KI 0.75 mg/ml, $MnSO_4.4H_2O$ 10.0 mg/ml, $H_3BO_3$ 3.0 mg/ml, $ZnSO_4.7H_2O$ 2 mg/ml, $Na_2MoO_4.2H_2O$ 0.25 mg/ml, $CuSO_4.5H_2O$ 0.025 mg/ml, $CoCl_2.6H_2O$ 0.025 mg/ml, Inositol 100 mg/ml, Nicotinic acid 1.0 mg/ml, Pyridoxine.HCl 1.0 mg/ml, Thiamine.HCl 10.0 mg/ml, Glucose 5 g/ml, Sucrose 25 g/ml, Xylose 250 mg/ml, Sodium pyruvate 5.0 mg/ml, Citric acid 10.0 mg/ml, Malic acid 10.0 mg/ml, Fumaric acid 10.0 mg/ml, N-Z-amine 500.0 mg/ml, 2,4-dichlorophenoxyacetic acid 1.0 mg/ml and Zeatine riboside 0.1 mg/ml, adjusted to pH 5.7 with KOH.

Figure 4:
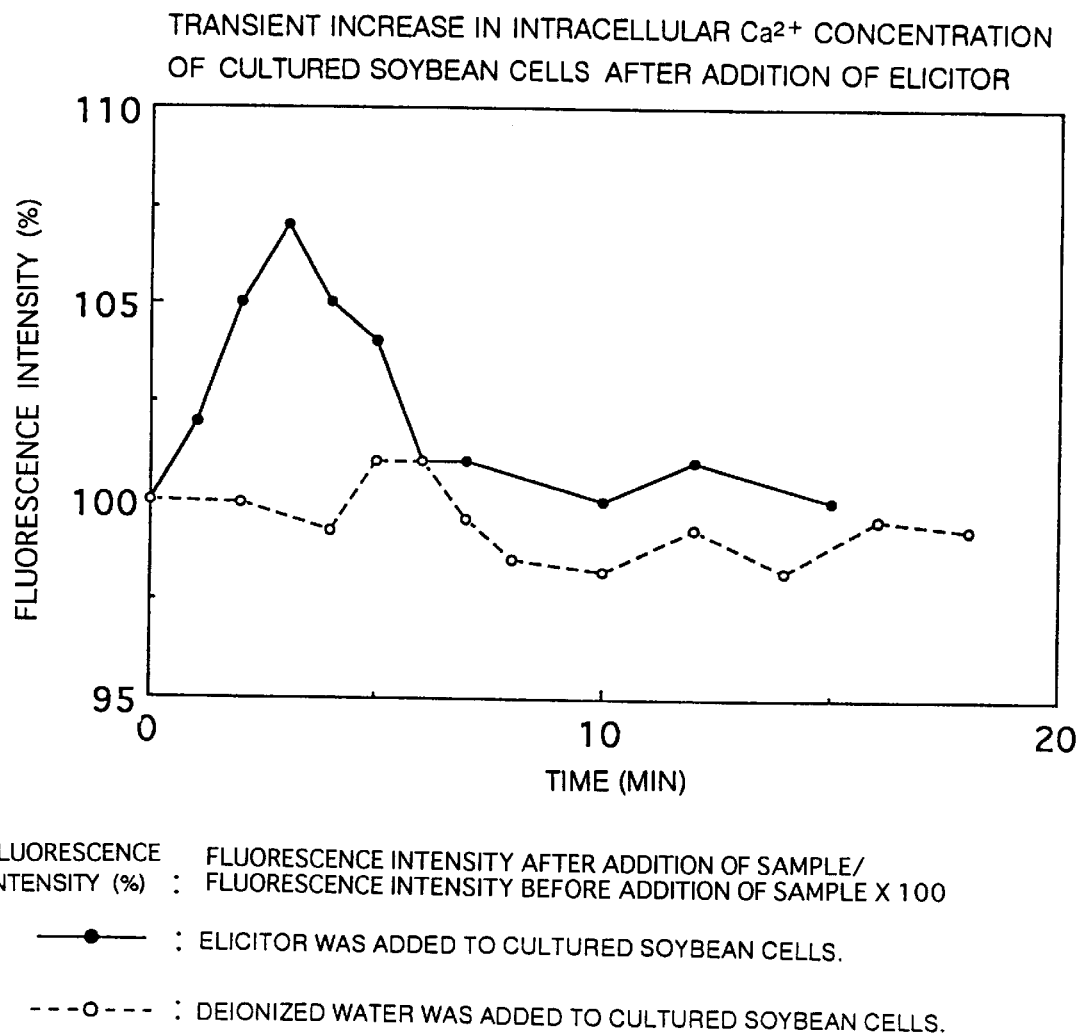
FIG. 4 shows a transient increase in intracellular $Ca^{2+}$ concentration after the addition of an elicitor to cultured soybean cells.

As a result of this experiment, about 7% transient increase in fluorescence intensity was observed in the cultured soybean cells 3 minutes after the addition of the elicitor, whereas no such change was observed after the addition of deionized water (FIG. 4). The results suggest that the phenomenon in which the binding of the ER to the glucan elicitor caused a transient inflow of $Ca^{2+}$ into cells could be observed in this experiment, thereby supporting the report that calcium ion plays an important role in the resistance reaction caused by the elicitor in cultured soybean cells. In the transformed cultured tobacco cells, about 10% transient increase in fluorescence intensity was observed 3 minutes after the addition of the elicitor, whereas no such change was observed after the addition of deionized water.

Figure 5:
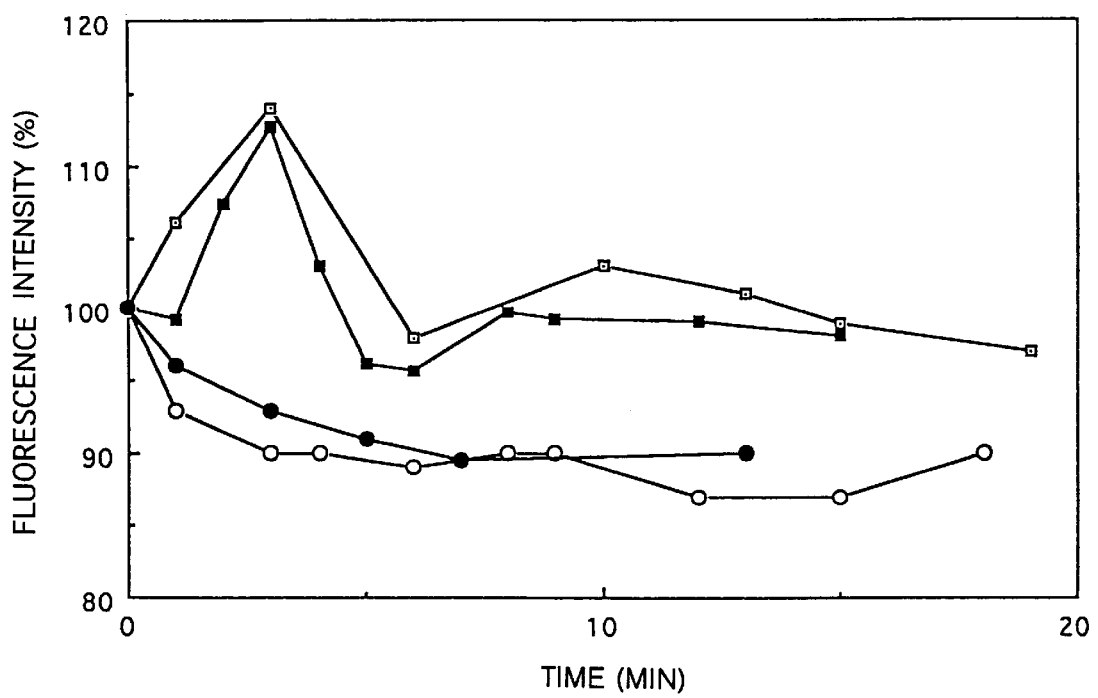
FIG. 5 shows a transient increase in intracellular $Ca^{2+}$ concentration after the addition of an elicitor to transformed cultured tobacco cells.

In the plasmid-containing cultured tobacco cells, none of the changes in fluorescence intensity that occurred in the transformed cultured tobacco cells was observed after the addition of the elicitor (FIG. 5).

These results show that plants other than soybean (e.g., tobacco), which are not reactive with the glucan elicitor acquire the reactivity by introducing the gene of the soybean-derived glucan elicitor receptor for ER expression. Although the signal transduction pathway of each plant has not been completely explicated, it is expected that plants other than tobacco will acquire the reactivity with the glucan elicitor (i.e., a transient increase in intracellular $Ca^{2+}$ concentration) by introducing the gene of the present ER for ER expression, thereby enabling the development of plants having resistance to a wide variety of fungi which use glucan as a mycelial wall component.

EXAMPLE 4

Expression of Soybean ER in *E. coli* and Determination of Elicitor-binding Domain 1) Expression of Elicitor-binding Domain in *E. coli*

A fused protein of a partial fragment of the soybean ER with a maltose-binding protein (MBP) was prepared with a Protein Fusion & Purification System (New England Biolabs Co.) in order to express the partial fragment of the soybean ER in *E. coli*. PCR was performed using pER23-1 as a template to give DNA fragments of various lengths. The primers were designed to produce the MBP and fused protein in cloning into plasmid pMAL-c2 (New England Biolabs Co.) by adding a BamHI site on the 5' side and a SalI site on the 3' side exterior to the DNA molecule encoding the full-length portion and fragments of soybean ER shown in FIG. 6. These primers were synthesized with an automatic nucleic acid synthesizer (Model 394 of Applied Biosystems Co.). The following primers were used in the amplification of the DNA chain.

Primer U35 5'-ATGGATCCATGGTTAACATCCAAACC-3' (SEQ ID NO:17);
Primer U36 5'-ATGGATCCGAATATAACTGGGAGAAG-3' (SEQ ID NO:18);
Primer U37 5'-ATGGATCCCCAGCATGGGGTAGGAAG-3' (SEQ ID NO:19);
Primer U38 5'-TAGTCGACTACTTCTCCCAGTTATATTC-3' (SEQ ID NO:20);
Primer U39 5'-TAGTCGACTACTTCCTACCCCATGCTGG-3' (SEQ ID NO:21);
Primer U40 5'-TAGTCGACTATTCATCACTTCTGCTATG-3' (SEQ ID NO:22);
Primer U41 5'-ATGGATCCGCCCCACAAGGTCCCAAA-3' (SEQ ID NO:23); and
Primer U42 5'-ATGGATCCAATGACTCCAACACCAAG-3' (SEQ ID NO:24)

The DNA molecule of pER23-1 (0.01 µg) was dissolved in 79 µl of distilled water. Either a combination of primers U5 and U7 or a combination of primers U10 and U12 (100 pmol each) and 0.5 µl of Taq DNA polymerase (TAKARA SHUZO CO., LTD.) were added to 8 µl of 2.5 mM dNTP in 10 µl of a 10×PCR buffer (attached to Taq DNA polymerase of TAKARA SHUZO CO., LTD.) to give a final amount of 100 µl. PCR reaction was performed with a Gene Amp PCR System 9600 (Perkin-Elmer Co.) by 30 cycles of 1) denaturation at 94° C.×30 seconds, 2) renaturation at 55° C.×30 seconds and 3) elongation at 72° C.×1 minute. After the reaction, 15 µl of the reaction solution was digested with restriction enzymes BamHI and SalI and electrophoresed on a 1% agarose gel.

The gel was stained with a 0.5 µg/ml ethidium bromide solution for 15 minutes. The band showing the expected specific amplification was sectioned while observing under UV light. The gel section was treated with Gene Clean II (Bio101 Co.) to collect a DNA-containing solution. The collected DNA fragments were cloned into the BamHI-SalI site of plasmid PMAL-c2 and the clones were introduced into *E. coli* DH5$_\alpha$.

2) Preparation of Soluble Protein Fraction from *E. coli*

The *E. coli* cells into which the plasmids were introduced were precultured in an expression medium [10 g/l tryptone (Gibco Co.), 5 g/l yeast extract (Gibco Co.), 5 g/l NaCl, 2 g/l glucose and 100 µg/ml ampicillin]. The precultured solution (0.4 ml) was added to 40 ml of the expression medium and cultured at 37° C. with shaking until $OD_{600}$ of 0.55 was reached. Isopropylthiogalactoside was added to the culture solution to give a final concentration of 0.3 mM and the shaking culture was continued for an additional 4 hours to induce expression. The *E. coli* was collected by centrifugation and the *E. coli* cells were washed with a washing buffer (20 mM Tris-HCl, pH 7.4, 200 mM NaCl and 1 mM EDTA). The cells were sonicated for a total of 2 minutes (15 sec×8). ZW3-12 was added to the sonicated cells to give a final concentration of 0.25% and the mixture was incubated at 4° C. for 30 minutes. The supernatant was collected by centrifugation (10,000 rpm, 5 minutes) to give an *E. coli* soluble protein fraction. The expression of the fused protein was confirmed by an immunoblotting technique using an anti-maltose-binding protein antibody (New England Biolabs Co.).

3) Elicitor-binding Experiment

The elicitor-binding activity was determined as follows:

A complex of an elicitor and tyramine (TOKYO KASEI KOGYO CO., LTD.) was synthesized by the method of Jong-Joo Cheong (The Plant Cell (1991) 3: 127). The elicitor-tyramine complex was labelled with iodine-125 using chloramine T. The resulting sample (protein amount <800 µg) was suspended in 500 µl of an assay buffer (50 mM Tris-HCl pH7.4, 0.1 M saccharose, 5 mM $MgCl_2$, 1 mM PMSF and 5 mM EDTA) and incubated at 0° C. for 2 hours. The iodine-labelled elicitor-tyramine complex in an amount of 100 nM (70 Ci/mmol) was added to the suspension and the mixture was incubated at 4° C. for 2 hours. The reaction solution was filtered through Whatman GF/B (as treated with a 0.3% aqueous solution of polyethylenimine for at least 1 hour) and washed 3 times with 5 ml of an ice-cold buffer (10 mM Tris-HCl pH 7.0, 1 M NaCl, 10 mM $MgCl_2$). The radio activity retained on the filter membrane was counted with a gamma counter (count A). In order to eliminate the effect of non-specific binding, the same procedure as above was performed except that 17 µM of the elicitor was added to the same sample, the mixture was suspended in the assay buffer and the suspension was incubated at 0° C. for 2 hours. The obtained count was subtracted from the count A to give a count (Δ cpm) of elicitor-specific binding. The resulting count (Δ cpm) was divided by the total number of counts and then multiplied by the total amount of the elicitor used in the experiment to calculate the amount of the elicitor-binding protein (in moles).

Figure 6:
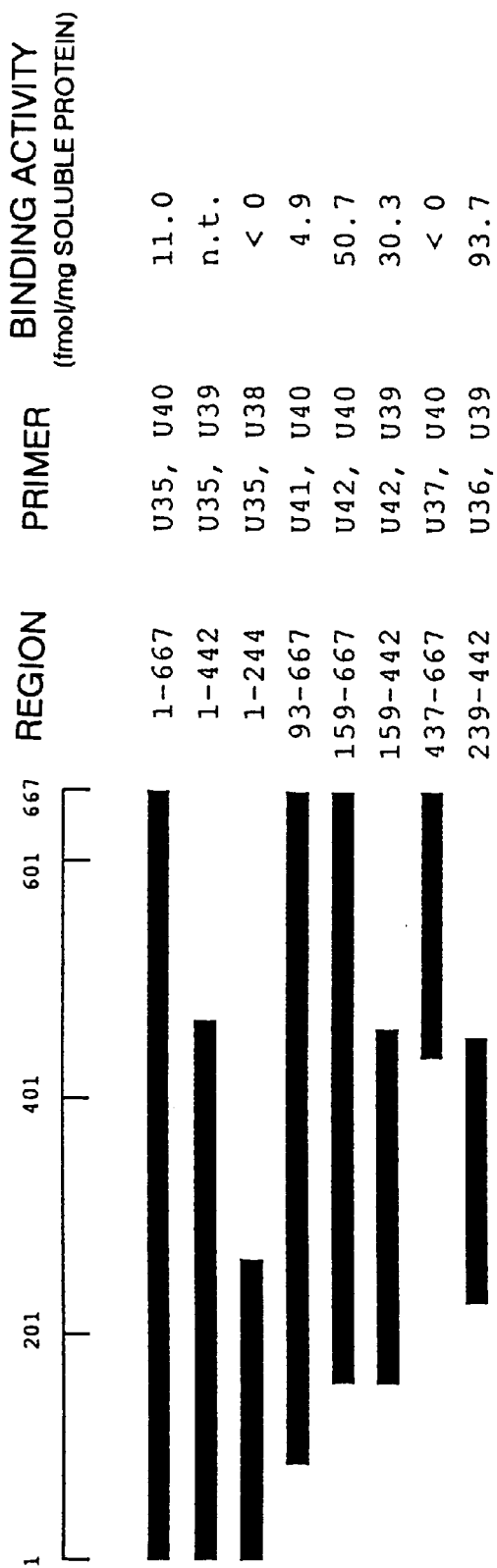
FIG. 6 shows elicitor-binding activities of full- or partial length glucan elicitor receptor expressed in E. coli.

As a result, a specific binding to the elicitor was observed in the E. coli transformed with the DNA molecule encoding the ER (FIG. 6). Hence, it was reconfirmed that the obtained gene encoded a protein having the elicitor-binding activity and it was revealed that there was an elicitor-binding domain in the 239–442 amino acid sequence of SEQ ID NO:1.

EXAMPLE 5
Inhibition of Binding of Glucan Elicitor to Elicitor-binding Protein in Soybean Cotyledon Membrane Fraction and Inhibition of Accumulation of Phytoalexin in Soybean Cotyledon by Antibody against Elicitor-binding Domain
1) Expression of Elicitor-binding Domain in E. coli A fused protein of an elicitor-binding domain derived from the ER with a maltose-binding protein (MBP) was prepared with a Protein Fusion & Purification System (New England Biolabs Co.) in order to express a large amount of the elicitor-binding domain in E. coli. PCR was performed to produce a DNA molecule encoding the elicitor-binding domain. The following primers were synthesized with an automatic nucleic acid synthesizer (Model 394 of Applied Biosystems Co.):
Primer U36 5'-ATGGATCCGAATATAACTGGGAGAAG-3' (SEQ ID NO:25); and
Primer U39 5'-TAGTCGACTACTTCCTACCCCATGCTGG-3' (SEQ ID NO:26)

The DNA molecule of pER23-1 (0.01 μg) was dissolved in 79 μl of distilled water. Either a combination of primers U5 and U7 or a combination of primers U10 and U12 (100 pmol each) and 0.5 μl of Taq DNA polymerase (TAKARA SHUZO CO., LTD.) were added to 8 μl of 2.5 mM dNTP in 10 μl of a 10×PCR buffer (attached to Taq DNA polymerase of TAKARA SHUZO CO., LTD.) to give a final amount of 100 μl. PCR was performed with a Gene Amp PCR System 9600 (Perkin-Elmer Co.) by 30 cycles of 1) denaturation at 94° C.×30 seconds, 2) renaturation at 55° C.×30 seconds and 3) elongation at 72° C.×1 minute. After the reaction, 15 μl of the reaction solution was digested with restriction enzymes BamHI and SalI and electrophoresed on a 1% agarose gel.

Figure 7:
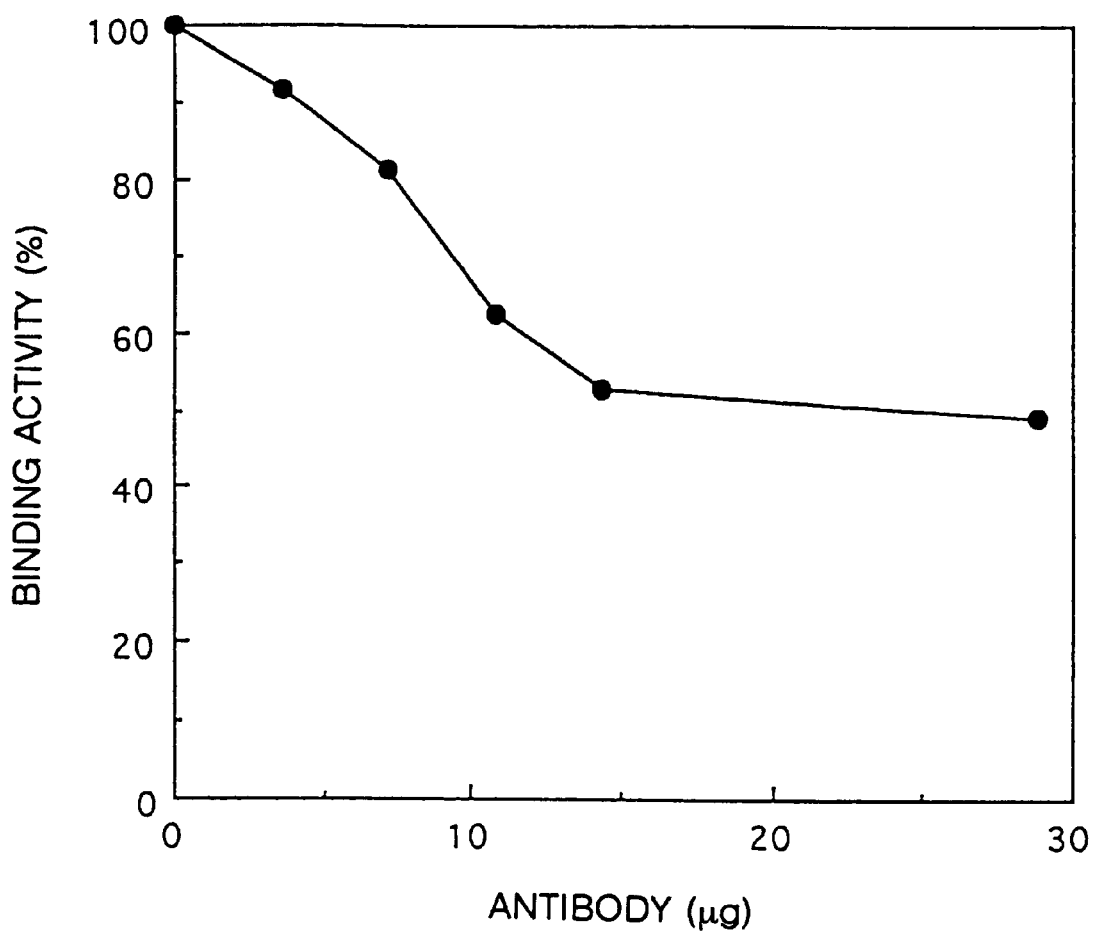
FIG. 7 shows the inhibition of the binding of an elicitor with an elicitor binding protein in a soybean cotyledon membrane fraction by an antibody against an elicitor-binding domain.

The gel was stained with a 0.5 μg/ml ethidium bromide solution for 15 minutes. The band showing specific amplification was sectioned while observing under UV light. The gel section was treated with Gene Clean II (Bio101 Co.) to collect a DNA-containing solution. The collected DNA fragments were cloned into the BamHI-SalI site of plasmid pMAL-c2 and the clones were introduced into E. coli DH5$_\alpha$.
2) Purification of the Fused Protein Expressed in E. coli and Production of Antibody The E. coli cells transformed with the plasmids were precultured in an expression medium (10 g/l tryptone (Gibco Co.), 5 g/l yeast extract (Gibco Co.), 5 g/l NaCl, 2 g/l glucose and 100 μg/ml ampicillin) overnight. The precultured solution (150 ml) was added to 1.5 L of the expression medium and cultured in a Sakaguchi flask at 37° C. with shaking until $OD_{600}$ of 0.55 was reached. Isopropylthiogalactoside was added to the culture solution to give a final concentration of 0.3 mM and the shakeculture was continued for an additional 4 hours to induce expression. The E. coli was collected by centrifugation and the E. coli cells were washed with a washing buffer (20 mM Tris-HCl, pH 7.4, 200 mM NaCl and 1 mM EDTA). The cells were sonicated for a total of 2 minutes (15 sec×8). A soluble protein fraction was obtained by centrifugation. From this fraction, a MBP-fused protein was purified with an amylose resin. A MBP- and an elicitor-binding domain were cleaved with factor Xa and the elicitor-binding domain was purified by gel filtration column chromatography. The purified protein was injected twice into a mouse at the abdominal cavity for immunization by the method of E. Harlow and D. Lane (Antibody (1988) Cold Spring Harbor Co., pp. 53–137). After the increase in titer was confirmed by an ELISA method, the ascites was obtained and subjected to precipitation with 50% saturated ammonium sulfate and treated with Protein A Sepharose (Pharmacia Co.) to produce a purified antibody. In the treatment with Protein A Sepharose, the antibody was bound to Protein A Sepharose with 0.1 M sodium phosphate (pH 8.0) and eluted with 0.1 M citric acid (pH 3.5). It was confirmed by an immnoblotting that the obtained antibody recognized only the ER protein in soybean.
3) Preparation of Soybean Cotyledon Membrane Fraction A soyben cotyledon membrane fraction was prepared as follows:

To soybean cotyledons cultured on soil for 9 days (wet weight: 36 g), 47 ml of an ice-cooled buffer (25 mM Tris-HCl, pH 7.0, 30 mM $MgCl_2$, 2 mM dithiothreitol, 2.5 mM sodium metabisulfite, 1 mM PMSF) was added and homogenized with a waring blender, followed by fractionation through centrifugation to form a precipitate of the cotyledon membrane fraction; the procedure was the same as in the preparation of the soybean root membrane fraction described in Section 2) of Example 1. The cotyledon membrane fraction was suspended in an ice-cooled buffer (10 mM Tris-HCl, pH 7.4, 0.1 M sucrose, 5 mM $MgCl_2$, 1 mM PMSF, 5 mM EDTA) and stored at −80° C.
4) Measurement of Inhibition of Glucan Elicitor Binding to Elicitor-binding Protein of Soybean Cotyledon Membrane Fraction The elicitor-binding activity was determined as follows:
A complex of an elicitor and tyramine (TOKYO KASEI KOGYO CO., LTD.) was synthesized by the method of Jong-Joo Cheong (The Plant Cell (1991) 3: 127). The elicitor-tyramine complex was labelled with iodine-125 using chloramine T. The soybean cotyledon membrane faction (100 μl, 820 μg) was suspended in 500 μl of an assay buffer (50 mM Tris-HCl pH7.4, 0.1 M saccharose, 5 mM $MgCl_2$, 1 mM PMSF and 5 mM EDTA) and incubated at 0° C. for 2 hours. The iodine-labelled elicitor-tyramine complex in an amount of 714 ng (143 nM; 70 Ci/mmol) was added to the suspension and the mixture was incubated at 4° C. for 2 hours. The reaction solution was filtered through Whatman GF/B (as treated with a 0.3% aqueous solution of polyethylenimine for at least 1 hour) and washed 3 times with 5 ml of an ice-cold buffer (10 mM Tris-HCl pH 7.0, 1 M NaCl, 10 mM $MgCl_2$). The radio activity retained on the filter membrane was counted with a gamma counter (count A). In order to eliminate the effect of non-specific binding, the same procedure as above was performed, except that 100 times mole (75 μg, 15 μM) of a cold elicitor was added to the the sample, the mixture was suspended in the assay buffer and the suspension was incubated at 0° C. for 2 hours. The obtained count was subtracted from the count A to give a count (Δ cpm) of elicitor-specific binding. Counts of binding obtained by adding 3.6, 7.1, 10.8, 14.4 and 28.8 μg of the purified antibody rather than the cold elicitor were subtracted from the count A. The resulting values were compared with that for the cold elicitor and expressed as the percentage, with the count (Δ cpm) of elicitor-specific binding being taken as 100% (FIG. 7). The addition of 28.8 μg of the antibody resulted in the inhibition of the binding of elicitor by about 51%. The results confirmed that the antibody against the elicitor-binding domain inhibited the binding of the elicitor to the elicitor-binding protein.

5) Inhibition of Accumulation of Phytoalexin by Antibody against Elicitor-binding Domain The amount of phytoalexin accumulated by the action of glucan elicitor was measured with soybean cotyledons by the method of M. G. Hahn et al. ((1992) Molecular Plant Pathology Volume II A Practical Approach, IRL Press, pp. 117–120).

Figure 8:
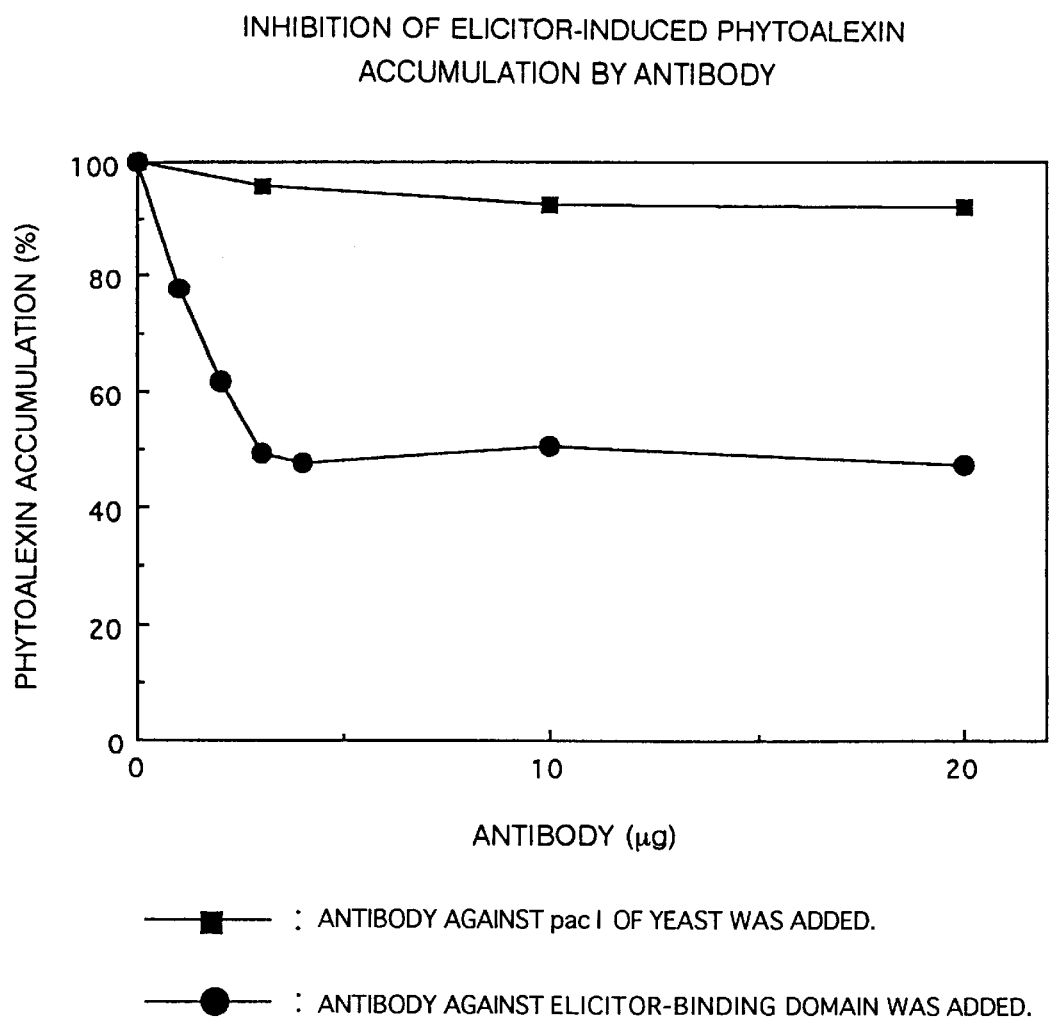
FIG. 8 shows the inhibition of an elicitor-induced phytoalexin accumulation in soybean cotyledons by an antibody against an elicitor-binding domain.

A purified antibody against the elicitor-binding domain (0, 1, 2, 3, 4, 10 and 20 μg/25 μl/cotyledon) or a purified antibody against yeast-derived dsRNAse, pac 1 (4, 10 and 20 μg/25 μl/cotyledon) as a control was added to soybean cotyledons and the mixture was incubated for 1 hour. Glucan elicitor (200 ng/25 μl/cotyledon) was added to the soybean cotyledons and the mixture was incubated for 20 hours to determine whether the accumulation of phytoalexin by the action of glucan elicitor was inhibited by the antibody. The amount of phytoalexin accumulation induced by the addition of elicitor subsequent to the addition of the antibody was expressed as the percentage, with the amount of phytoalexin accumulation by the sole addition of the elicitor being taken as 100% (FIG. 8). When the antibody against the elicitor-binding domain was added in an amount of 20.0 μg per soybean cotyledon, the amount of phytoalexin accumulation decreased by about 53%. In the control, the amount of phytoalexin accumulation changed little even when the antibody against pac 1 was added in an amount of 20.0 μg per soybean cotyledon. These results showed that the obtained gene did not encode a mere elicitor-binding protein but encoded the ER inducing a resistance reaction in soybean.

EXAMPLE 6
Transfer of ER Gene into Tobacco Plants

The soybean-derived ER gene was transferred into tobacco as described below, and the expression of the gene was confirmed.

1) Construction of Plant Expression Vector Plasmid

Plasmid pER23-1 is digested with BamHI and SalI to give an ER gene fragment sandwiched between the sites of the two restriction enzymes. This fragment is inserted into a plant vector to be described below. In a separate step, a plant expression-type binary plasmid pBI121 (Clonetech) was digested with restriction enzymes BamHI and SacI. Then, the following linker DNAs synthesized with an automatic nucleic acid synthesizer were annealed and ligated to the digested binary plasmid, which was introduced into *E. coli* DH5$_\alpha$. Desired plasmid pBIlinker was selected from the obtained clones.

5'-CTAGAGGATCCGGTACCCCCGGGGTCGACGAGC T-3' (SEQ ID NO: 27)
5'-CGTCGACCCCGGGGGTACCGGATCCT-3' (SEQ ID NO: 28)

The gene fragment described above was inserted between the cauliflower mosaic virus 35S promoter and the terminator of nopaline synthase (BamHI-SalI) in the resultant plasmid pBIlinker to produce a vector to be introduced into plants (pBI-ER).

2) Introduction of pBI-ER into Agrobacterium

*Agrobacterium tumefaciens* LBA4404 (Clonetech) was inoculated into 50 ml of YEB medium (containing 5 g of beef extract, 1 g of yeast extract, 1 g of peptone, 5 g of sucrose and 2 mM MgSO$_4$ per liter, pH 7.4) and cultured at 28° C. for 24 hours. Then, the cells were harvested by centrifugation at 3,000 rpm and 4° C. for 20 minutes. The cells were washed three times with 10 ml of 1 mM Hepes-KOH (pH 7.4), once with 3 ml of 10% glycerol and finally suspended in 3 ml of 10% glycerol to give an Agrobacterium into which DNA of interest was to be introduced.

Fifty μl of the thus obtained bacterium suspension and 1 μg of plasmid pBI-ER were placed in a cuvette, to which an electrical pulse was applied at 25 μF, 2500 V and 200 Ω using an electroporation apparatus (Gene Pulser; BioRad) to introduce the plasmid DNA into the Agrobacterium. The resultant solution was transferred to an Eppendorf tube, followed by the addition of 800 μl of SOC medium (containing 20 g of tryptone, 5 g of yeast extract, 0.5 g of NaCl, 2.5 mM KCl, 10 mM MgSO$_4$, 10 mM MgCl$_2$ and 20 mM glucose per liter, pH 7.0). The bacterium was subjected to stationary culture at 28° C. for 1.5 hours. Fifty μl of the resultant culture solution was plated on YEB agar medium (agar 1.2%) containing 100 ppm kanamycin and cultured at 28° C. for 2 days.

A single colony was selected from the resultant colonies, and plasmid DNA was prepared from that colony by an alkaline method. This plasmid DNA was digested with an appropriate restriction enzyme, and the resultant DNA fragments were fractionated by 1% agarose gel electrophoresis and analyzed. As a result, it was confirmed that the plasmid DNA contained plasmid pBI-ER. This *Agrobacterium tumefaciens* is designated Agro-ER.

3) Transformation of Tobacco

The Agro-ER strain described above was cultured under shaking in LB liquid medium containing 50 ppm kanamycin at 28° C. for 2 hours. Cells were harvested by centrifuging 1.5 ml of the culture solution at 10,000 rpm for 3 minutes and washed with 1 ml of LB medium to remove the kanamycin. Then, the cells were harvested by further centrifugation at 10,000 rpm for 3 minutes and re-suspended in 1.5 ml of LB medium to give a bacterium suspension for infection.

In infecting a tobacco variety Bright Yellow with the bacterium, young leaves were collected from a germ-free plant. These leaves were aseptically cut into pieces 1 cm$^2$ in size with a surgical knife, placed on the Agrobacterium suspension with back of each leaf facing up, and shaken gently for 2 minutes. Thereafter, the leaf pieces were placed on a sterilized filter paper to remove excessive Agrobacterium. Whatman No. 1 filter paper (φ 7.0 cm) was placed on MS-B5 medium (containing 1.0 ppm benzyladenine, 0.1 ppm naphthaleneacetic acid and 0.8% agar) (Murashige, T. and Skoog, F. Plant Physiol., 15: 473, (1962)) in a culture dish. The leaf pieces were placed upon this filter paper with the back of each leaf facing up. The culture dish was sealed with a PARAFILM (American National Can), and then the leaf pieces were cultured at 25° C. for 2 days through cycles of 16 hours under light and 8 hours in the dark. Subsequently, the leaf pieces were transferred onto MS-B5 medium containing 250 ppm claforan and cultured in the same manner for another 10 days in order to remove the Agrobacterium. The leaf pieces were further transferred onto MS-B5 medium containing 250 ppm claforan and 100 ppm kanamycin and cultured in the same manner for another 7 days. During this period, the regions surrounding the leaf pieces changed to callus, yielding shoot primordia. After culturing for another 10 days, elongated shoots were placed on MS-HF medium (benzyladenine- and naphthaleneacetic acid-free MS-B5 medium) containing 250 ppm claforan and 100 ppm kanamycin. After culturing for 10 days, those shoots which were rooting were placed on MS-HF medium containing 250 ppm claforan in a plant box as kanamycin resistant transformants.

4) PCR and Immunoblot Analysis of Genomic DNA from the Transformant Tobacco

In order to confirm that the gene of interest was transferred into the transformant, a PCR was performed. The following primers were synthesized with an automatic nucleic acid synthesizer (Applied Biosystems; Model 394) and used in the PCR.

Primer ER1 5'-CACCTTCAGCAACAATGGTT-3' (SEQ ID NO: 29)

Primer ER2 5'-CTATTCATCACTTCTGCTAT-3' (SEQ ID NO: 30)

DNA was extracted from the kanamycin resistant transformant tobacco and examined. Genomic DNA was extracted as described below. Briefly, 20 mg of tobacco leaves was crushed with a plastic bar in 200 μl of an extraction buffer (0.5 M NaCl, 50 mM Tris-HCl, pH 8, 50 mM EDTA). Then, 60 μl of 20% polyvinyl pyrrolidone (mean molecular weight: 40 kDa) and 52 μl of 10% SDS were added and heated at 65° C. for 30 minutes. Subsequently, 40 μl of 5 M potassium acetate was added, and the resultant mixture was left on ice for 30 minutes. Then, the mixture was centrifuged to recover the supernatant; 180 μl of isopropyl alcohol was then added to recover the DNA as a precipitate. After washing with 70% ethanol, the DNA was dissolved in 150 μl of TE solution (10 mM Tris-HCl, pH 8, 1 mM EDTA, 1 μg/ml RNase A). To 79 μl of distilled water, 1 μl of this DNA solution, 10 μl of 10× PCR buffer (attachment to Taq DNA polymerase; Takara Shuzo), 8 μl of 2.5 mM dNTP, 100 pmol each of primers ER1 and ER2, and 0.5 μl of Taq DNA polymerase (Takara Shuzo) were added to make a 100 μl solution. With this solution, a PCR was performed as follows. As a reaction apparatus, Gene Amp PCR System 9600 (Perkin-Elmer) was used. First, denaturation reaction was performed at 94° C. for 5 minutes. Then, 30 cycles of 1) denaturation at 94° C. for 30 seconds, 2) renaturation at 55° C. for 30 seconds and 3) extension at 72° C. for 1 minute were performed. After the reaction, 15 μl of the reaction solution was electrophoresed on 1% agarose gel. The gel was stained with a 0 5 μg/ml ethidium bromide solution for 15 minutes and examined under UV light. By confirming a specific DNA fragment of about 2 kbp which was expected to be amplified, it was confirmed that the gene of interest has been incorporated into the tobacco genomic DNA.

Immunoblot analysis was also performed to check for the expression of the gene of interest. Briefly, 20 mg of tobacco leaves was crushed with a plastic bar in 100 μl of an ice-cooled extraction buffer (0.1 M Tris-HCl, pH 7.5, 1 mM PMSF). Then, 50 μl of 3× SDS-PAGE sample buffer (30% glycerol, 3% β-mercaptoethanol, 3% SDS, 0.19 M Tris-HCl, pH 6.8, 0.001% BPB) was added and heated at 100° C. for 5 minutes. The resultant mixture was centrifuged at 12,000 rpm for 5 minutes to recover the supernatant. A portion (15 μl) of the extracted protein was subjected to SDS-polyacrylamide gel electrophoresis and transferred onto a PVDF membrane (Millipore). Immunoblotting was performed on this membrane using the anti-ER mouse antibody prepared in Example 5 as a primary antibody, anti-mouse immunoglobulin alkaline phosphatase-labeled antibody (Jackson) as a secondary antibody and also an alkaline phosphatase coloring substrate (Wako Pure Chemical Industries) to assay the expression of the ER protein. There were a plurality of plants expressing various amounts of the ER protein. From these plants, those expressing a large quantity of the ER protein were selected and subjected to a hypersensitive reaction test and a fungus resistance test.

EXAMPLE 7

Hypersensitive Reaction Test of the Tobacco Transformant

Induction of hypersensitive reaction by a soybean elicitor was examined using leaves of the tobacco transformants in which high expression of the ER protein had been confirmed in Example 6, as well as leaves of non-transformed tobacco plants and those tobacco plants transformed with the vector (pBI121) alone as controls.

Leaves of tobacco plants grown in a green house were cut off at the petiole and placed in a light-transmissive plastic box. A piece of silicone tube 5 mm in diameter and 5 mm in height was put on the upper surface of each leaf so that a solution could be retained. This tube piece was allowed to retain a chemically synthesized elicitor (β-D-glucohexaoside) [N. Hong and T. Ogawa (1990), Tetrahedron Lett. 31: 3179; released from Prof. Ogawa of the Institute of Physical and Chemical Research and the University of Tokyo] dissolved in a buffer solution (3 mM sodium bicarbonate, 4 mM sodium acetate, pH 8.0) or the buffer solution alone such that the solution was kept in contact with the surface of each leaf. The leaves were cultured under excessive moisture to prevent drying of the solution through cycles of 16 hours under light and 8 hours in the dark at 25° C. for 7 day. After the culture, the silicone tube was removed, and the induction of synthesis of tobacco phytoalexin was examined on a UV illuminator (Funakoshi). Nothing could be found from the combination of non-transformed tobacco and the chemically synthesized glucan elicitor or from the combination of tobacco plants transformed with the vector alone and the glucan elicitor. This means that tobacco cannot recognize this glucan elicitor. On the other hand, from the combination of tobacco TF1-11-1-15 transformed with the ER gene and the chemically synthesized glucan elicitor, accumulation of a remarkable amount of a fluorescent substance (phytoalexin) was recognized. Also, no changes were observed in controls, i.e., those combinations of the tobacco plants and the buffer solution alone or deionized water.

From these results, it was proved that, if the ER gene can be expressed in a host plant other than soybean, there is a possibility that the transformed host plant may acquire the ability to recognize a glucan elicitor which the non-transformed host cannot recognize. The present invention provides not only a possibility to change the plant recognition of a substance, but also a mechanism by which a plant can recognize plant pathogens such as fungi having a glucan structure in their cell walls or the like. As a result, resistant reactions such as induction of phytoalexin closely involved in disease resistance is elicited in the plant. Elicitation of such resistant reactions is important for breeding disease resistant plants.

EXAMPLE 8

Fungus Resistance Test of the Tobacco Transformant

The tobacco transformants in which high expression of the ER protein had been confirmed in Example 6 were selfed or crossed with glucanase-expressing tobacco plants (Japanese Unexamined Patent Publication No. 4-320631) to harvest seeds, the subsequent generation.

1) Resistance to *Phytophthora nicotianae*

A strain conserved at Hokkaido University (subcultured in PDA medium from Difco) was transferred to an oatmeal agar and cultured at 26° C. for 4 days. The growing end portion of the mycelium spreading all over the medium was punched with a cork borer to form mycelium disks, which were used as an inoculant. The oatmeal agar medium used in this experiment was prepared as follows. One hundred grams of oatmeal powder was suspended in 1 liter of water, heated at 58° C. for 1 hour and filtered with gauze. To the filtrate, 20 g of agar was added and autoclave-sterilized. Then, the resultant mixture was dispensed into culture dishes for use as a medium.

Figure 9:
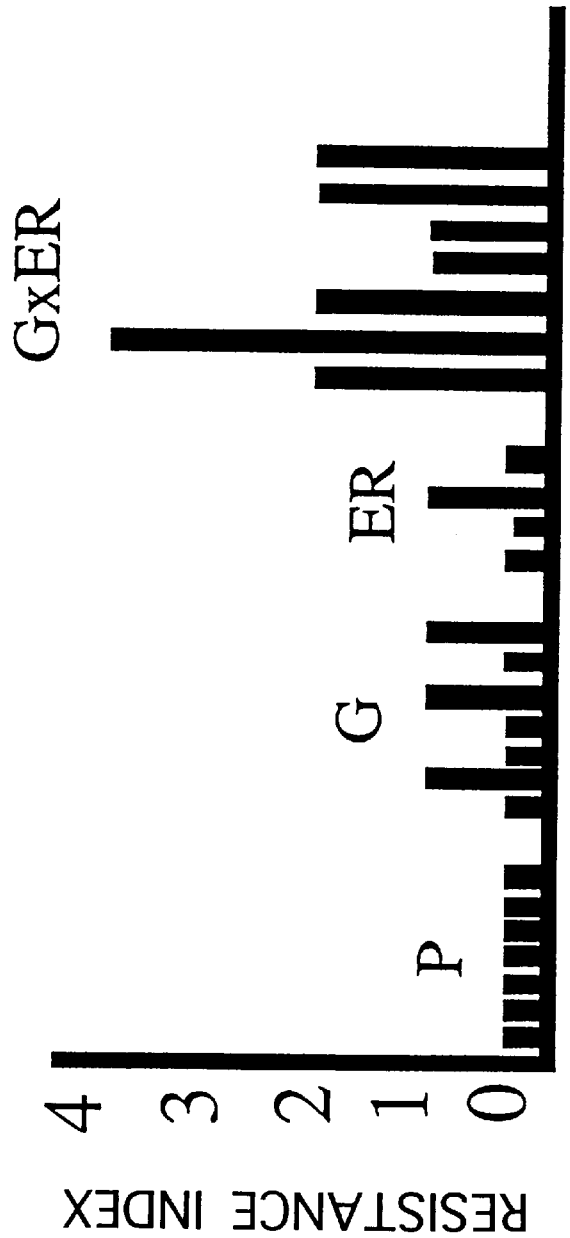
FIG. 9 shows the resistance of transformed tobacco plants to P. nicotianae.
Figure 11:
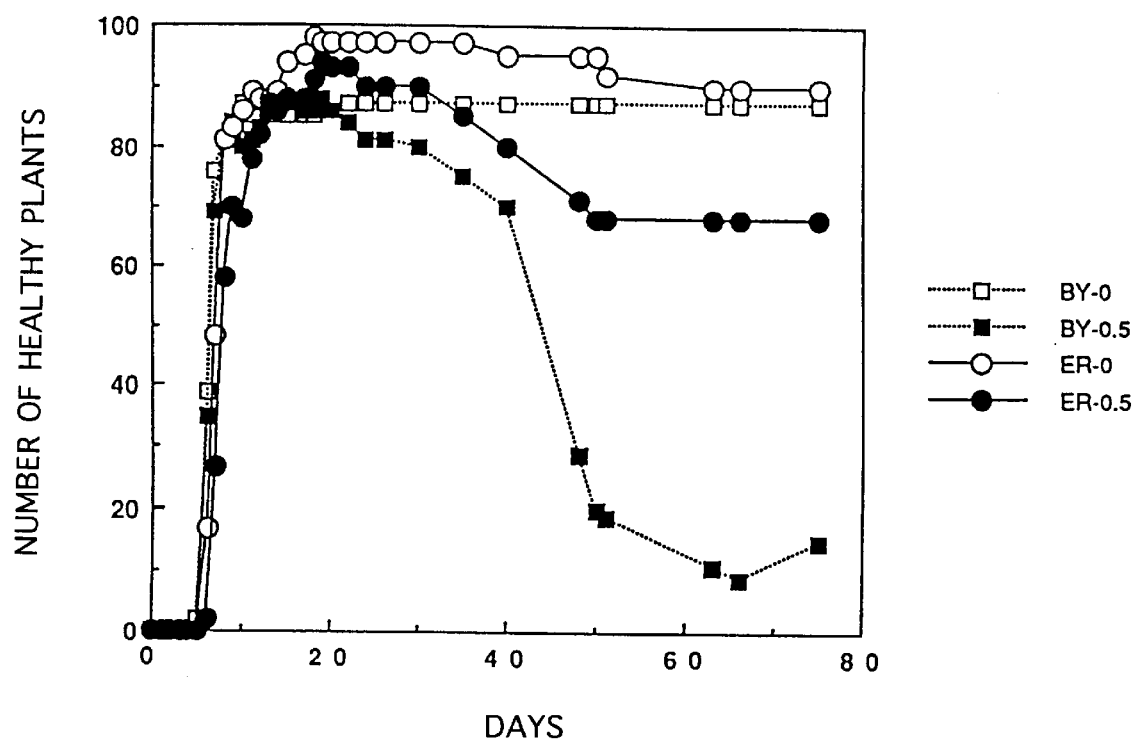
FIG. 11 shows the resistance of transformed tobacco plants to R. solani.

Seedlings obtained from the above-mentioned seeds were tested for expression of ER based on the method described in Example 6. Then, the fungus was inoculated into wounds of those seedlings in which a remarkable expression of ER had been confirmed. Briefly, leaves cut off from tobacco plants about 2 months after germination were placed on a moisturized filter paper in a plastic box. Ten needles tied up together were applied 30 times at one point on both the right and the left side in each of the leaves, yielding punctured wounds in the form of a concentric circle. A small amount of deionized water was applied to the wounds, and then the mycelium disk was inoculated into each wound. Thereafter, the leaves were left at 25° C. for 96 hours. The results of this test are shown in FIG. 9 and Table 3. The resistance of each tobacco leaf tested is shown with a resistance index. The resistance indexes are as follows. "4": no disease symptom; "3": up to 25% of the surface bears disease symptoms on both sides of the leaf; "2": up to 50% of the surface bears disease symptoms on both sides of the leaf; "1": up to 75% of the surface bears disease symptoms on both sides of the leaf; "0": 75% or more of the surface bears disease symptoms on both sides of the leaf.

was observed and, finally, the number of healthy individuals for each of the tested tobacco plants was counted (FIGS. 10 and 11).

As a result, the formation and expansion of lesions were observed in control plants (non-transformed tobacco); the number of healthy individuals decreased sharply; and most of the individuals withered. On the other hand, in ER-expressing transformants, lesions were hardly observed or delay in the development of disease symptoms was observed (FIG. 10). Therefore, it is believed that the resistance to fungi was improved by the transfer of the ER gene.

3) Fungus Resistance Test using Zoospores of *Phytophthora nicotianae*

In addition to the fungus resistance test by needle inoculation described in section 1) of Example 8, another fungus resistance test was conducted by inoculating a zoospore suspension. A fungus strain conserved at Hokkaido University (subcultured in PDA medium from Difco) was transferred to an oatmeal agar and cultured at 25° C. in the dark for 1 week. The oatmeal agar was prepared by suspending 100 g of oatmeal powder in 1 liter of water, heating at 58° C. for 1 hour and filtering with gauze; to the filtrate, 20 g of agar was added, autoclave-sterilized and dispensed into culture dishes for use as a medium. From the resultant mycelial flora, disks were punched with a cork borer 6 mm in diameter. The disks were placed on 9 cm plastic culture dishes at regular spacings (7 disks/dish). To each dish, 25 ml of a soybean decoction medium (obtained by grinding 400 g of green soybean, filtering the resultant material with

TABLE 3

Resistance to *P. nicotianae*

| Tobacco plant individual No. | P-1 | 2 | 3 | 4 | 5 | 6 | 7 | G-1 | 4 | 6 | 7 | 8 | 9 | 10 |
|---|---|---|---|---|---|---|---|---|---|---|---|---|---|---|
| Resistance index | 0 | 0 | 0 | 0 | 0 | 0 | 0 | 0 | 1 | 0 | 0 | 1 | 0 | 1 |

| Tobacco plant individual No. | ER-51 | 55 | 56 | 57 | GxER-10 | 11 | 16 | 24 | 28 | 34 | 38 |
|---|---|---|---|---|---|---|---|---|---|---|---|
| Resistance index | 0 | 0 | 1 | 0 | 2 | 4 | 2 | 1 | 1 | 2 | 2 |

P: tobacco transformed with pBI121 (control)
G: glucanase-expressing tobacco
ER: ER-expressing tobacco
GxER: glucanase/ER-coexpressing tobacco As a result, the formation and expansion of lesions were observed in control plants (plants transformed with pBI121 and plants expressing glucanase alone) whereas the expansion of lesions was not so remarkable in most of the transformants coexpressing glucanase and ER. Therefore, it is believed that the resistance to fungi was improved by the transfer of the ER gene.

2) Resistance to *Rhizoctonia solani*

A strain conserved at Gifu University (*Rhizoctonia solani* AG3 M strain; released from Prof. Hyakumachi of Gifu University; subcultured in PDA medium from Difco) was inoculated into an autoclave-sterilized mixture of barley grains and deionized water (50:50 by volume), cultured at 24° C. for 10 days and dried for 10 days. Then, the barley grains were milled by a coffee maker and mixed well with a soil (river sand:vermiculite:peat moss=2:2:1) at a ratio of 0.5% (w/w). The test seeds were sown on this mixture and grown through cycles of 16 hours under light and 8 hour in the dark at 25° C. under a humidity of 60–80%. Their growth gauze and adding distilled water to the filtrate to make a 1 liter solution, followed by autoclave sterilization) was added, and the disks were cultured at 25° C. in the dark for 3 days. After confirming that mycelial mat was formed on almost all over the culture dishes, the medium was discarded. The mycelial mat was washed with an aqueous Petri solution (1 mM KCl, 2 mM $Ca(NO_3)_2$, 1.2 mM $MgSO_4$, 1 mM $KH_2PO_4$) three or four times to remove the medium components as completely as possible. Finally, the mycelial mat was washed once with a soil extract (prepared by adding water to 11.5 g of field soil to make a volume of 1 liter, filtering the mixture and sterilizing in an autoclave). After swishing water off, the mycelial mat was left at 15° C. under lighting for several days until its surface became slightly dry. It has been found for the first time that this drying treatment is very important for the formation of a large quantity of zoosporangia of the fungus. To the thus formed zoosporangia, the soil extract was added and left to stand at 15° C. under lighting for 2–3 hours. After confirming that a sufficient amount of zoospores was formed, the zoospores were collected to give an inoculant.

Figure 12:
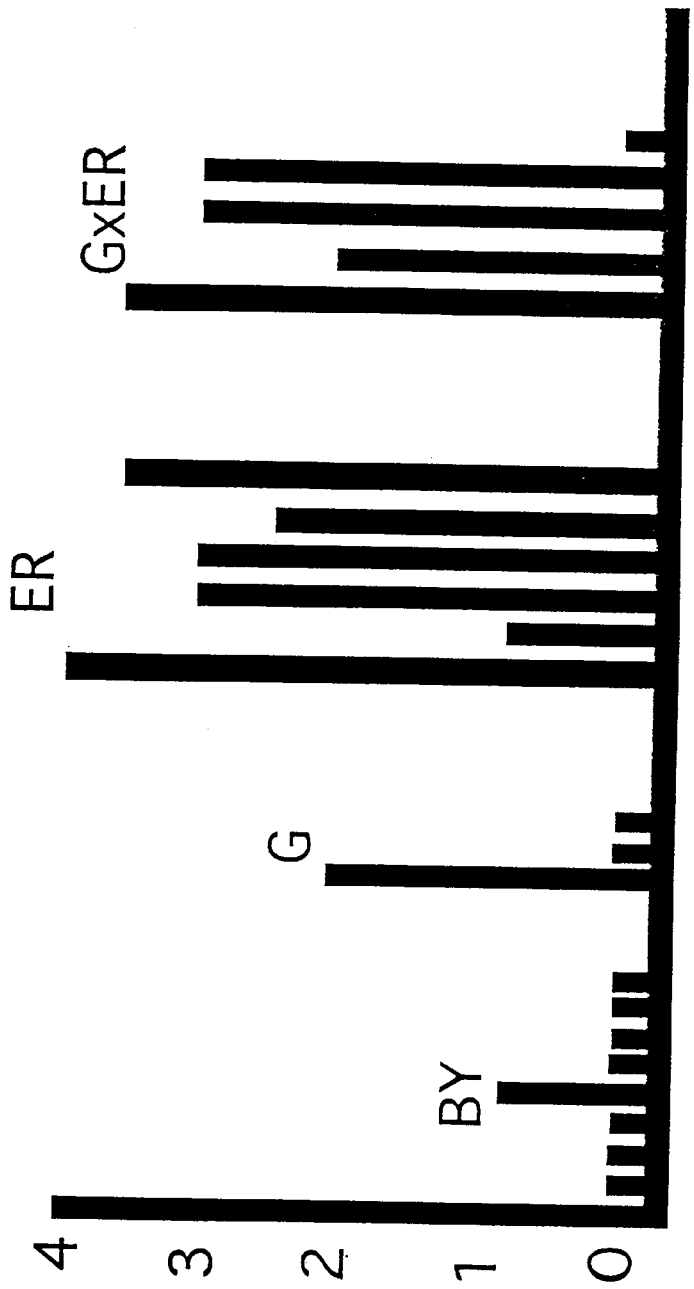
FIG. 12 shows the resistance of transformed tobacco plants to P. nicotianae in an inoculation test using zoospores from P. nicotianae.

The zoospores were inoculated to those plants in which a remarkable expression of ER had been confirmed based on the method described in Example 6. Briefly, leaves of tobacco plants about 4 months after germination were cut off and placed on a moisturized filter paper in a plastic box. A silicone ring cut into about 5 mm in length was placed on both the right and the left side of each of the leaves. Then, 100 µl of a zoospore suspension (3–5×10$^5$ zoospores/ml) was added into the silicone ring with a micropipette to thereby inoculate the zoospores to the surface of the tobacco leaf. Then, each leaf was left at 25° C. for 144 hours. The results of this test are shown in FIG. 12 and Table 4.

The resistance of each tobacco leaf tested is shown with a resistance index. The resistance indexes are as follows. "4": no disease symptom; "3.5": lesions are restricted to the inoculation site; "3": up to 25% of the half leaf bears disease symptoms; "2.5": up to 37.5% of the half leaf bears disease symptoms; "2": up to 50% of the half leaf bears disease symptoms; "1": up to 75% of the half leaf bears disease symptoms; "0": more than 75% of the half leaf bears disease symptoms.

TABLE 4

Resistance to Zoospores of *P. nicotianae*

| Tobacco plant individual No. | BY-1 | 2 | 3 | 4 | 5 | 6 | 7 | 8 | G-1 | 2 | 3 |
|---|---|---|---|---|---|---|---|---|---|---|---|
| Resistance index | 0 | 0 | 0 | 1 | 0 | 0 | 0 | 0 | 2 | 0 | 0 |

| Tobacco plant individual No. | ER-1 | 2 | 3 | 4 | 5 | 6 | GxER-1 | 2 | 3 | 4 | 5 |
|---|---|---|---|---|---|---|---|---|---|---|---|
| Resistance index | 4 | 1 | 3 | 3 | 2.5 | 3.5 | 3.5 | 2 | 3 | 3 | 0 |

BY: non-transformed tobacco (control)
G: glucanase-expressing tobacco
ER: ER-expressing tobacco
GxER: glucanase/ER-coexpressing tobacco As a result, the formation and expansion of lesions were observed in control plants (non-transformed tobacco and tobacco expressing glucanase alone) whereas the expansion of lesions were inhibited in most of the transformants expressing ER alone or ER and glucanase. Therefore, it is believed that the resistance to fungi was improved by the transfer of the ER gene.

EXAMPLE 9

Cloning of Novel Kidney Bean Glucanase

1) Preparation of Soybean mRNA

Kidney bean (Hirasaya Fancy Saitou) seeds (Takayama Seed Co.) were cultured on vermiculite for 12 days and then treated with ethylene for 48 hours according to the method of U. Vogeli et al. [Planta (1988) 174: 364] in order to induce the expression of glucanase. The plants were frozen in liquid nitrogen and stored at −80° C. until use. According to the method of Ishida et al. ("Cell Technology Laboratory Manipulation Manual" authored by Ishida and Misawa, Kodansha Scientific), 2.35 mg of total RNA was obtained from 12 g of frozen kidney bean powder.

Subsequently, 1.0 mg of the thus obtained total RNA was used for purification with Oligo (dT) Cellulose (Pharmacia) according to the manual and then 31.5 µg of purified poly(A)+RNA was obtained.

2) Preparation of Kidney Bean cDNA Library cDNA was synthesized from 5 µg of the poly(A)+RNA with Time Saver cDNA Synthesis Kit (Pharmacia) and random hexamer primers. The synthesized cDNA fragments were ligated to lambda phage vector λ gt10 (Stratagene) with T4 DNA ligase (Takara Shuzo). Subsequently, the phage vectors were packaged to form phage particles with Gigapack (Stratagene) using a DNA mixed solution to thereby prepare a kidney bean cDNA library of about 1×10$^5$ pfu.

3) Preparation of a Screening Probe

Based on the report of B.V. Edington et al. [Plant Molecular Biology (1991) 16:81] on the cloning of kidney bean glucanase cDNA, PCR primers were prepared as follows: sense primer: 5'-CAAATGTTGTGGTGAGGGATG GCC-3' (SEQ ID NO: 31) and antisense primer: 5'-AAATGTTTCTCTATCTCAGGACTC -3' (SEQ ID NO: 32). An RT-PCR was performed with these primers according to the method of Ishida ("Gene High Expression Experiment Manual", Ishida and Ando (Eds.), Kodansha Scientific) to give a PCR fragment of about 300 bp. This fragment was subcloned into the EcoRV site of pBluescriptSKII+ (Stratagene). For the cDNA synthesis, 1 mg of total RNA and 0.5 mg of random hexamer primers (Takara Shuzo) were used. The DNA sequence of the insert (0.3 kbp) in the subclone plasmid was determined. As a result, the DNA sequence was found to be identical with the glucanase cDNA reported by B. V. Edington et al.(supra). This plasmid DNA was digested with HindIII and EcoRV, and fractionated by agarose gel electrophoresis. The insert DNA was purified with Gene Clean II (Bio 101) to give a probe for screening the kidney bean cDNA library prepared in 2) above.

4) Screening and Cloning of the Library by Hybridization

The DNA fragment obtained as a screening probe was labelled with [α-$^{32}$P]dCTP using Megaprime DNA labelling kit (Amersham) according to the manual, and the reaction solution was subjected to the subsequent hybridization experiment.

*E. coli* C600 hfl (Invitrogen) was transfected with the kidney bean cDNA library prepared in 2) above, and inoculated into L medium supplemented with 10 mg/ml MgCl$_2$ in a culture dish about 15 cm in diameter to form a total of about 1×10$^5$ plaques. The plaques were blotted to a nylon membrane (GeneScreen(+); NEN DuPont). The membrane was reacted with the $^{32}$P-dCTP-labelled glucanase cDNA fragment, and positive phages detected by autoradiography were screened again in the same manner to give one phage clone.

Figure 13:
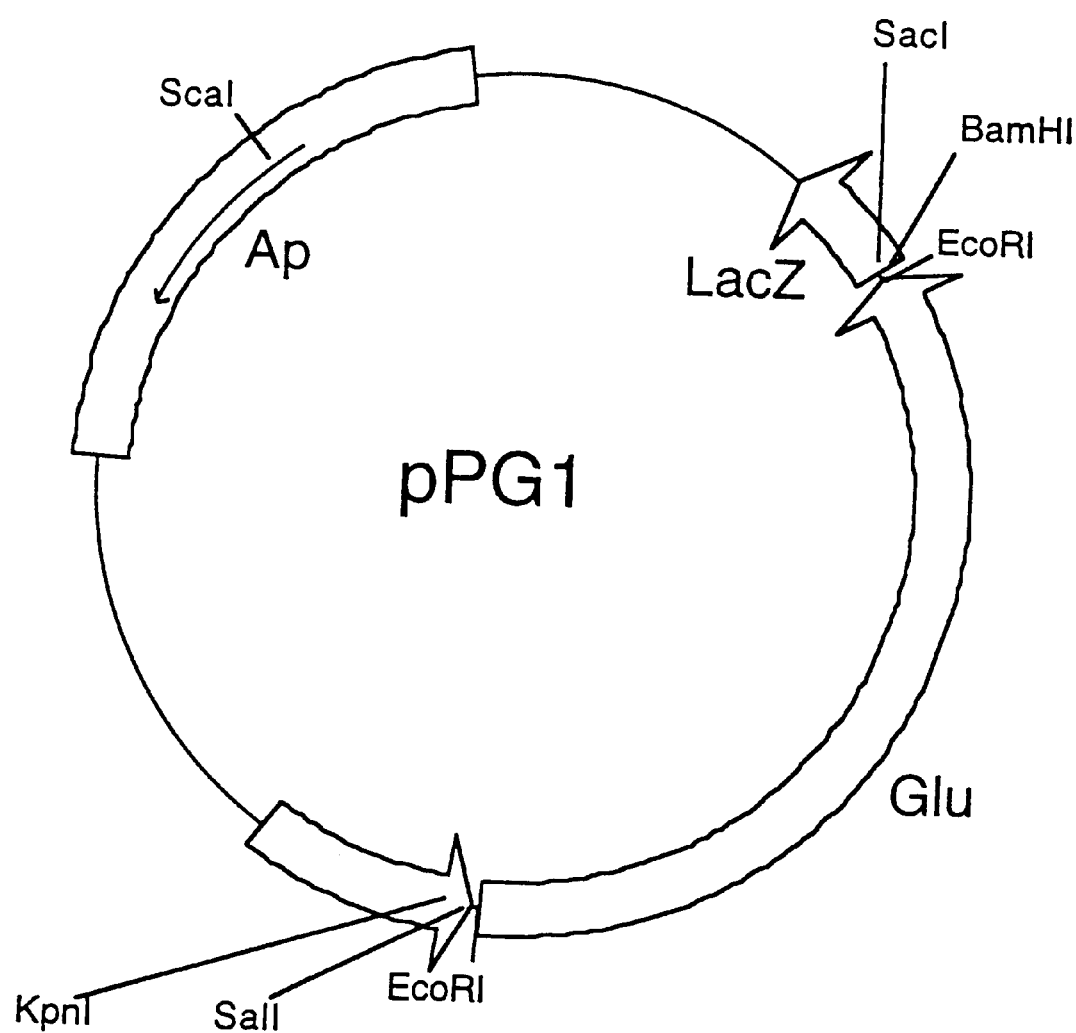
FIG. 13 shows the structure of plasmid pPG1.

The λ phage DNA was purified with Lambda Sorb (Promega) from a solution of the positive clone isolated in the hybridization experiment. Five micrograms of this DNA was digested with EcoRI and fractionated by 1% agarose gel electrophoresis to cut out an about 1.2 kb band. This band was treated with Gene Clean II (Bio 101) to recover a solution containing the DNA, which was subcloned into the EcoRI site of vector pBluescriptII KS+ (Stratagene). FIG. 13 shows the structure of plasmid pPG1.

5) Determination of the Nucleotide Sequence of the DNA Coding for Kidney Bean Glucanase The DNA of the plasmid into which the glucanase cDNA had been cloned was sequenced in both orientations with a fluorescence sequencer by preparing a series of plasmids having deletions at intervals of ca. 200–300 bp, using Kilosequence Deletion Kit (Takara Shuzo). The resultant nucleotide sequence for the DNA is shown in SEQ ID NO: 33. As a result, the DNA fragment was found to contain an ORF of 993 bp starting from a nucleotide sequence corresponding to an amino acid sequence that was predictably to be a signal sequence; it is presumed that 331 amino acid residues are encoded in the ORF. This amino acid sequence is shown in SEQ ID NO: 34.

As a result of a search using BLAST Protein Search, the amino acid sequence deduced from the resultant nucleotide sequence was found to be a completely novel sequence. Compared with the amino acid sequence reported previously by B. V. Edington et al. [Plant Molecular Biology (1991) 16:81], there was 49% homology (excluding the portion which appeared to be a signal sequence). Besides, it had 51% homology in full length to the soybean-derived amino acid sequence reported by Y. Takeuchi et al. [Plant Physiol. (1990) 93:673]. Since the deduced amino acid sequence exhibits high homology to the amino acid sequences of the previously reported glucanases, it was expected that the resultant DNA sequence would also encode a glucanase. It was also expected that, unlike previously reported kidney bean glucanases, the glucanase under discussion was of an extracellular secreting type since the deduced amino acid sequence had a would-be signal sequence at its N-terminal while lacking a would-be vacuole targeting sequence at its C-terminal.

EXAMPLE 10
Expression of the Kidney Bean Glucanase
1) Construction of Plasmid pGST-PG1
  PCR sense primer: 5'-GGAATTCCGAATCTGTGGGTGTGTGTTAT-3' (SEQ ID NO: 35) and antisense primer: M13 reverse sequence primer (SEQ ID NO: 36) were designed so that the kidney bean glucanase sequence [excluding the signal sequence, i.e. Met(1)-Val(21) at the N-terminal] could be ligated downstream from glutathione-S-transferase expression vector (Pharmacia; pGEX-4T-3) in an in-frame fashion. With these primers, a PCR was performed on 0.1 mg of a template plasmid pPG1 DNA using EX-Taq DNA polymerase (Takara Shuzo) (annealing temperature=50° C.; 20 cycles). The amplified PCR fragments were digested with EcoRI and fractionated by agarose gel electrophoresis to give a DNA fragment of about 1 kbp. This fragment was purified with Gene Clean II and subcloned into the EcoRI site of pGEX-4T-3 expression vector using JM109 competent cells (Toyobo) (pGST-PG1).
2) Expression in E. coli BL21

The plasmid DNA was purified from the subclone obtained in 1) above and re-transferred into E. coli BL21 competent cells (Molecular Cloning, Cold Spring Harbor Laboratory Press). The E. coli BL21 was released from Prof. Masayuki Yamamoto, the Department of Science, the University of Tokyo.
3) Purification of GST-Fused Glucanase An overnight culture (4 ml) of the E. coli obtained in 1) above was transferred into 200 ml of 2×YT medium containing 100 mg/ml ampicillin and cultured at 37° C. for 1.5 hours. IPTG (Takara Shuzo) was added thereto to give a final concentration of 0.1 mM, and the cells were cultured for another 4 hours. The cells were harvested from the culture solution by centrifugation at 10,000 rpm and 4° C. for 10 minutes.

According to the Gene Expression Experiment Manual (supra), approximately 1 mg of glutathione-S-transferase/glucanase fusion protein (molecular weight: about 62 kDa) was purified using Glutathione Sepharose (Pharmacia).
4) Determination of Glucanase Activity The glucanase activity of the purified glutathione-S-transferase/glucanase fusion protein was determined by the following procedure. Briefly, an enzymic reaction solution was incubated at 37° C. The reaction was terminated at 0, 10, 20 and 30 minutes from the start of the reaction, and the liberated glucose was quantitatively determined by the method of Nelson [N. Nelson, J. Biol. Chem. (1944) 153, 375]. The enzymic reaction solution was composed of 0.5 ml of 50 mM acetate buffer (pH 5.5), 2.5 mg of laminarin as a substrate, and 0, 0.51 or 5.1 µg of the glutathione-S-transferase/glucanase fusion protein as an enzyme.

As a result, glucose was liberated from laminarin in a manner dependent on both enzyme concentration and reaction time (see FIG. 14). Thus, it was made clear that the newly cloned cDNA has glucanase activity. This suggests the possibility that the glucanase under consideration can also be utilized for improving plants' resistance to fungi, like the soybean-derived glucanase encoded by SEQ ID NO: 4.

Industrial Applicability

According to the present invention, a plant into which a DNA sequence coding for a glucan elicitor receptor has been transferred and which expresses the glucan elicitor receptor, as well as a method for creating the plant are provided.

The plant of the present invention has high resistance to fungi.

What is claimed is:

1. An isolated glucan elicitor receptor, comprising
   (a) an amino acid sequence as shown in SEQ ID NO:1, or
   (b) an amino acid sequence comprising residues 239–442 of SEQ ID NO:1.

2. An isolated DNA molecule containing a nucleotide sequence coding for the glucan elicitor receptor of claim 1.

3. The DNA molecule of claim 2, wherein the nucleotide sequence coding for the glucan elicitor receptor that has an amino acid sequence as shown in SEQ ID NO:1.

4. The DNA molecule of claim 2, wherein the nucleotide sequence coding for the glucan elicitor receptor is incorporated in plasmid pER23-1.

5. A vector containing the DNA molecule of claim 2.

6. A plant cell transformed with the DNA molecule of claim 2.

7. A transformed plant that has resistance to a pathogenic fungus, which expresses a DNA molecule according to claim 2.

8. The plant or its progeny of claim 7, wherein the DNA sequence encoding a glucan elicitor receptor contains a nucleotide sequence encoding an amino acid sequence as shown in SEQ ID NO:1 or comprises a nucleotide sequence as shown in SEQ ID NO: 2.

9. The plant or its progeny of claim 7, which is further transformed with a DNA sequence that encodes glucanase.

10. The plant or its progeny of claim 9, wherein said glucanase comprises an amino acid sequence as shown in SEQ ID NO:3 or 34, or a fragment thereof having glucanase activity.

11. The plant or its progeny of claim 9, wherein said DNA sequence that encodes glucanase is shown in SEQ ID NO:4 or 33.

12. The plant or its progeny of claim 7, wherein said pathogenic fungus contains glucan in a cell wall component.

13. The plant or its progeny of claim 7, wherein said pathogenic fungus belongs to the genus Phytophthora or Rhizoctonia.

14. The plant or its progeny of claim 7, wherein said plant is capable of being infected with a pathogenic fungus that contains glucan in a cell wall component.

15. The plant or its progeny of claim 7, wherein said plant is a Solanaceae or a Leguminosae.

16. The plant or its progeny of claim 10, wherein said glucanase comprises an amino acid sequence as shown in SEQ ID NO: 3 or 34.

* * * * *